United States Patent [19]
Piontek et al.

[11] Patent Number: 5,533,973
[45] Date of Patent: Jul. 9, 1996

[54] ALTERATION OF NUTRITIONAL PRODUCT DURING ENTERAL TUBE FEEDING

[75] Inventors: Carl J. Piontek, Powell; Terrence B. Mazer, Reynoldsburg; Joseph E. Walton, Westerville; Ronita K. Geckle, Columbus, all of Ohio

[73] Assignee: Abbott Laboratories, Abbott Park, Ill.

[21] Appl. No.: 372,624

[22] Filed: Jan. 13, 1995

[51] Int. Cl.$^6$ ............................................. A61M 37/00
[52] U.S. Cl. ........................... 604/83; 604/84; 604/85; 604/8; 604/890.1
[58] Field of Search ............................ 604/82, 83, 85, 604/56, 403, 408, 409, 405, 410, 415, 416, 251, 254, 255, 256, 257, 258, 260, 262, 890.1, 892.1, 87, 89, 8; 424/422–424, 468–475; 426/540

[56] References Cited

U.S. PATENT DOCUMENTS

| | | | |
|---|---|---|---|
| 4,839,281 | 6/1989 | Gorbach et al. | 435/34 |
| 4,927,411 | 5/1990 | Pastrone | 604/65 |
| 4,968,507 | 11/1990 | Zentner et al. | 424/465 |
| 4,985,017 | 1/1991 | Theeuwes | 604/92 |
| 5,147,646 | 9/1992 | Graham | 424/424 |
| 5,162,057 | 11/1992 | Akiyama et al. | 106/243 |
| 5,318,558 | 6/1994 | Linkwitz et al. | 604/892.1 |
| 5,324,280 | 6/1994 | Wong et al. | 604/892.1 |
| 5,385,545 | 1/1995 | Kriesl et al. | 604/82 |
| 5,385,546 | 1/1995 | Kriesl et al. | 604/85 |
| 5,385,547 | 1/1995 | Wong et al. | 604/87 |
| 5,484,410 | 1/1996 | Kriesel et al. | 604/89 |

FOREIGN PATENT DOCUMENTS

WO93/02558 of 1993 WIPO.

OTHER PUBLICATIONS

Potts et al, *Comparison of Blue Dye Visualization and Glucose Oxidase Test Strip Methods for Detecting Pulmonary Aspiration of Enteral Feedings in Intubated Adults*, Chest, vol. 103, Jan. 1993, pp. 117–121.

Nutrition In Critical Care, Zaloga, ed., Mosby–Year Book Inc., 1994, pp. 439–467.

*Primary Examiner*—Randall L. Green
*Assistant Examiner*—V. Alexander
*Attorney, Agent, or Firm*—Brian R. Woodworth

[57] ABSTRACT

An apparatus and method are disclosed for modifying a liquid enteral nutritional product during delivery thereof from a supply to a feeding tube delivering the modified liquid enteral nutritional product to the gastrointestinal tract of a patient. At least one beneficial agent not in controlled release dosage form in a useful, dose unit, amount, is disposed within a formulation chamber so as to be taken up in a liquid enteral nutritional product traversing the formulation chamber while feeding the modified nutritional product into the gastrointestinal tract of a patient. The beneficial additive(s) are selected from nutrients, medicaments, probiotics, or diagnostic agents, or mixtures thereof, each in a dosage form that is dispersible in the medium of the liquid enteral nutritional product in less than two hours.

26 Claims, 15 Drawing Sheets

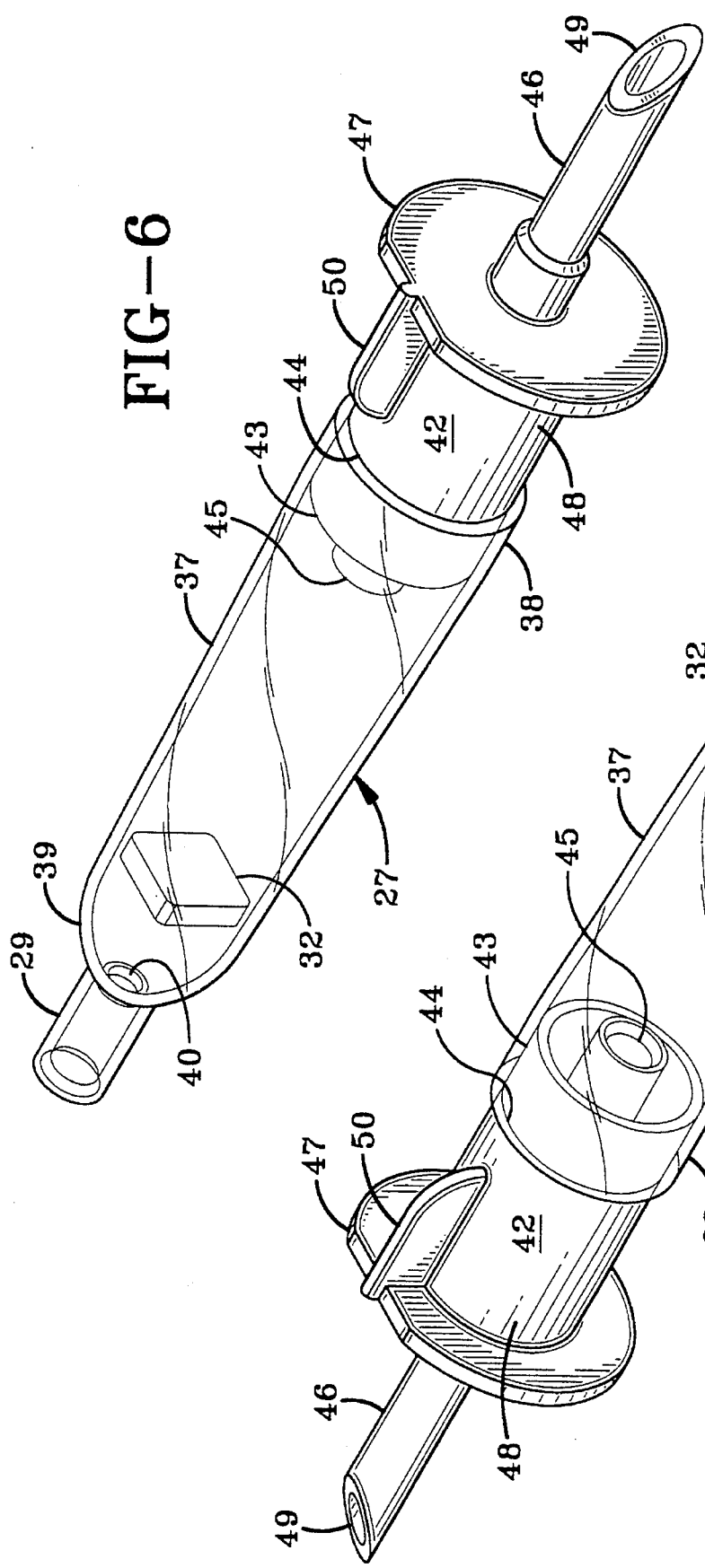

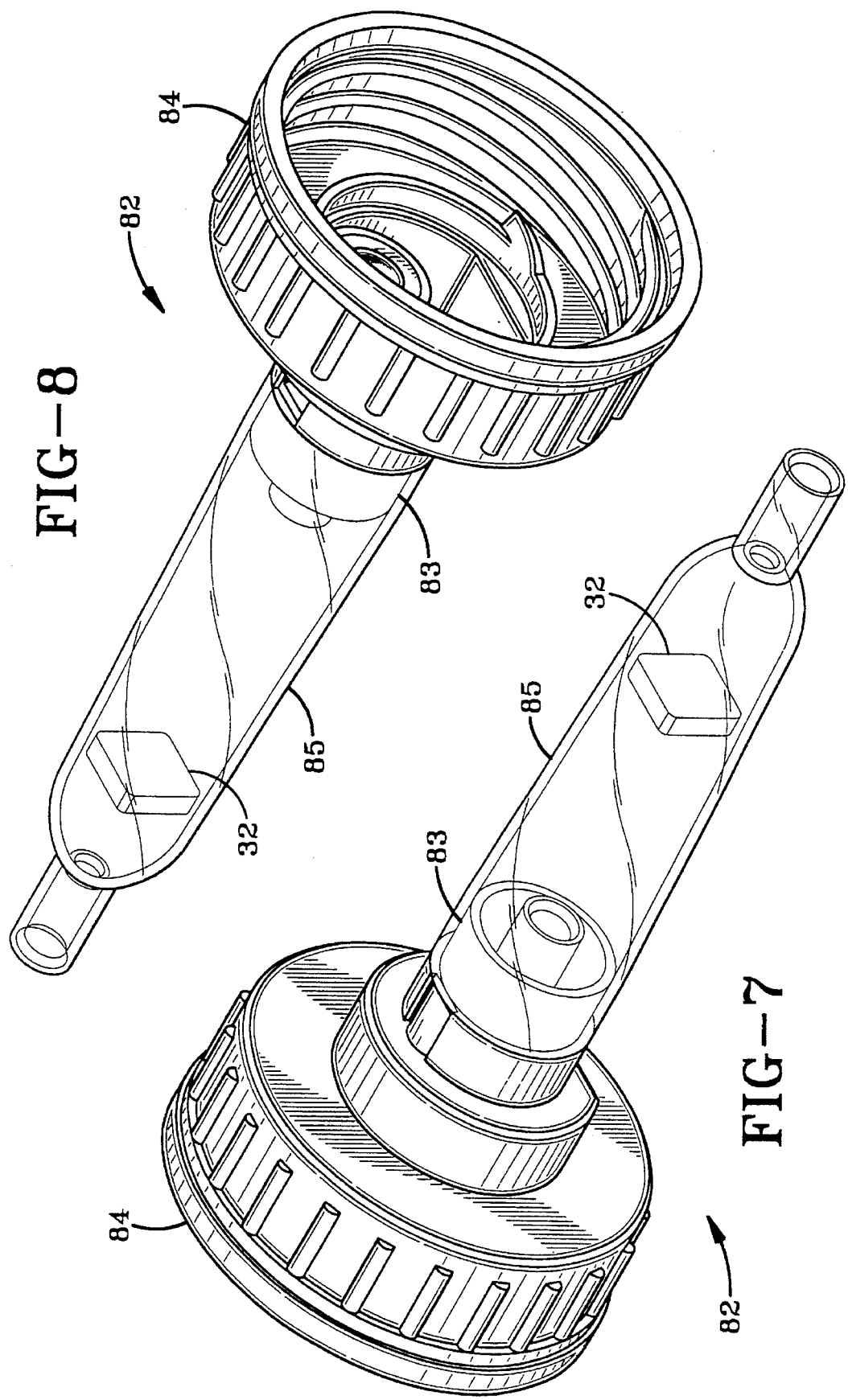

ALTERATION OF NUTRITIONAL PRODUCT DURING ENTERAL TUBE FEEDING

Field of the Invention

The invention relates to an apparatus and method for feeding liquid enteral nutritional products and particularly to modifying a liquid enteral nutritional product having a viscosity in the range of from 1 to about 300 centipoises (cps.) by adding ingredients during the feeding thereof into the gastrointestinal tract of a patient.

BACKGROUND OF THE INVENTION

The feeding of a liquid enteral nutritional product from a hangable container, such as a bottle or a plastic bag with a bottom outlet connecting to a drip chamber and the latter to a flexible tubing, or lumen, leading to a nasogastric tube or a feeding tube inserted through a gastrostomy or a jejunostomy, by gravity flow or aided by a pump, is well known. The liquid enteral nutritional product may be aseptically processed or terminally retorted, and may be supplied in a pre-filled, ready-to-hang container, or placed in such a container by a caregiver. However, the selection of diets, particularly special diets, from amongst the rather modest number of typically available liquid enteral nutritional products is limited. This narrows, as a practical matter, the choices of the attending physician as to diet modifications, temporary or long term, that might significantly benefit the patient. In view of the now-recognized importance of providing aseptic nutritional compositions, it can be seen that modified diets are not easily prepared without observing the stringent requirements needed to deliver an aseptic nutritional composition to the patient. The need to observe such requirements has heretofore militated against preparing small quantities of special diets designed for a specific patient.

Moreover, a number of nutrients as well as medicaments, diagnostic agents, and other ingredients such as probiotics, that at any given time might be desirable to orally administer to a patient are not stable during heat sterilization or may not be mutually compatible with other desired ingredients for an extended period of time, such as days or even months until used, and thus are not readily amenable to large scale preparation and consequent storage as the product moves through commerce.

Although it has been the practice for some time to use a container, such as a hangable container, to deliver a liquid enteral nutritional product through a drip chamber and connecting flexible tubing to a feeding device such as a feeding tube extending into the gastrointestinal tract of a patient, so far as is known, there has been no attempt to utilize the drip chamber as a formulation chamber in such a feeding system and to add ingredients such as medicaments or additional nutrients to a flowing enteral nutritional product at the time of administering the nutritional product to the gastrointestinal tract of a patient. Liquid enteral nutritional products currently on the market are described in the reference text "Nutrition In Critical Care", Gary P. Zaloga, ed., Mosby—Year Book Inc., St. Louis, Mo., 1994, at Chapter 24, authored by Barbara Hopkins, Part III, "Feeding", pp. 439–467. This reference indicates that complete nutrient compositions contain proteins, carbohydrates, fibers, fats, and vitamins and minerals in an aqueous medium.

SUMMARY OF THE INVENTION

A first aspect of the invention concerns an apparatus for modifying a liquid enteral nutritional product by adding ingredients thereto during delivery from a supply thereof, such as a hangable container, to a feeding tube delivering the liquid enteral nutritional product to the gastrointestinal tract of a patient.

The apparatus comprises:
- a formulation chamber, usually in the form of a drip chamber, connectable to a supply container of a liquid enteral nutritional product, normally an aqueous composition, so as to receive the -contents of the supply container therefrom, the formulation chamber having an inlet and an outlet,
- a useful quantity of at least one beneficial agent positioned within the formulation chamber so as to be contacted by, i.e., wetted by or immersed in, liquid enteral nutritional product traversing the formulation chamber during enteral feeding, each beneficial agent in the formulation chamber being dispersible in the medium of the liquid enteral nutritional product employed and being free from any controlled release coatings, or envelopes or mechanisms, i.e., being in non-controlled release dosage form, and each beneficial agent being selected from the group consisting of nutrients, medicaments, probiotics and diagnostic agents, and
- fluid communication means connecting the outlet of the formulation chamber to a tube for feeding the modified enteral nutritional product, containing the so-added at least one beneficial agent, into the gastrointestinal tract of a patient.

Each at least one beneficial agent that is to be added in non-controlled release dosage form during feeding is preferably added in at least a physiologically effective or diagnostically detectable amount or quantity and is selected from the group consisting of: nutrients; medicaments; probiotics; and diagnostic agents; and chemically and physiologically compatible combinations thereof; and any of the foregoing beneficial agents or combinations thereof together with at least one physiologically acceptable, and beneficial agent-compatible, marker dye or combination of dyes, the latter being in a sustained release dosage form, the dye or dyes being soluble in the medium of the liquid enteral nutritional product.

The formulation chamber is normally a conventional drip chamber which here serves also as the formulation chamber. If desired, one or more additional formulation chambers, that are not necessarily drip chambers, may be employed in order to introduce a larger amount of a given beneficial agent or mixture thereof, or to add additional beneficial agents and/or marker dye when not readily available in combination or not compatible during storage together in the formulation chamber of a feeding set. Each additional formulation chamber will have positioned therein, (1) a useful amount of at least one beneficial agent each of which is not in controlled release dosage form, or (2) at least one marker dye in sustained release dosage form, or (3) both at least one beneficial ingredient, each of which is not in controlled release dosage form, and, at least one marker dye in controlled release dosage form. Each additional formulation chamber may be connected in series as part of the fluid communication means. In each formulation chamber the liquid enteral nutritional product flows over the contents therein. If desired, two supply containers may be used in parallel with the inlets of respective formulation chambers connected to respective supply containers and with the respective outlets of the formulation chambers connected by fluid communication means such as flexible tubing to a "Y" connector. The parallel flows of modified liquid enteral nutritional product are joined into a single stream in the "Y" connector and directed by additional fluid communication means to the feeding tube of a patient. Each marker dye or marker dye mixture employed is introduced from a controlled release dosage form. Preferably, each controlled release dosage form unit is shaped or held in such a manner as to prevent or avoid the dosage form unit blocking flow out of the drip chamber or formulation chamber in which it is positioned.

The combination of (1) a formulation chamber, ordinarily in the form of a drip chamber, (2) fluid communication means, and (3) a quantity of at least one beneficial agent as herein defined, in non-controlled release dosage form, and with or without a marker dye or dyes in controlled release dosage form, with the quantity of at least one beneficial agent together with or without marker dye disposed in the formulation chamber, or merely accompanying the formulation chamber and supplied together, constitutes a useful kit. The kit is used for drawing a liquid enteral nutritional product from a supply container, such as a hangable container, and modifying the liquid enteral nutritional product by adding thereto a quantity of one or more beneficial agents with or without marker dye as the nutritional product is flowing from the supply container and feeding the modified nutritional product into a feeding tube leading into the gastrointestinal tract of a patient. If the at least one beneficial agent supplied as part of a kit is not already positioned in the formulation chamber it is readily manually placed therein, ordinarily prior to connecting the apparatus to the hangable supply container from which the liquid enteral nutritional product is to be drawn.

In a further aspect of the invention, the invention concerns a method of preparing a special diet for a patient comprising modifying a liquid enteral nutritional product during the flow thereof from a supply container containing such product to a feeding tube leading into the gastrointestinal tract of the patient. More specifically, the method comprises the steps of:

A providing an apparatus comprising:
  a formulation chamber having an inlet and an outlet, the inlet being connectable in fluid communication to a supply container of a liquid enteral nutritional product;
  a quantity of at least one beneficial agent disposed in the formulation chamber so as to be wetted by or immersed in a liquid enteral nutritional product traversing therethrough, each beneficial agent being selected from the group consisting of: nutrients; medicaments; probiotics; and diagnostic agents; and a chemically and physiologically compatible combination of such beneficial agents; and any of the foregoing agents or combinations of agents together with at least one compatible and physiologically acceptable marker dye in controlled release dosage form, each marker dye being dispersible in the medium of the liquid enteral nutritional product being modified; and each beneficial agent being not in controlled release dosage form; and
  fluid communication means capable of operatively connecting the outlet of the formulation chamber to a device, such as a feeding tube, for feeding a liquid enteral nutritional product into the gastrointestinal tract of the patient;

B. providing a supply container containing a liquid enteral nutritional product;

C. placing the apparatus in communicative series in the fluid flow between the supply container and the device for feeding; and, D. flowing the liquid enteral nutritional product through the apparatus wherein the nutritional product becomes modified and thence into the device for feeding.

In a modification of this method which may be especially useful in tailor-making a diet for a patient, the apparatus provided includes, in communicative series, one or more additional formulation chambers, that are not necessarily drip chambers, but which each have positioned therein a quantity of at least one beneficial agent, as herein defined, and the chambers are connected and positioned so as to permit the flow of the liquid enteral nutritional product over each beneficial agent to contact it or even immerse it dynamically, i.e., immerse it in a quantity of liquid that constantly turns over, in order to introduce a larger amount of given beneficial agent or mixture of beneficial agents than would be supplied readily in just one formulation chamber, or to add additional beneficial agents not readily available in combination or not compatible together in the same container or packaging or carrier envelope during storage prior to use.

If desired, or needed, a pump may be used to flow or help flow the modified liquid enteral nutritional product into the feeding device or tube, for example, when it is not convenient to hang or otherwise locate the supply container in an elevated position relative to the patient, or, when the nutritional product is rather viscous and flows slowly by gravity flow.

BRIEF DESCRIPTION OF THE DRAWINGS

The present invention will be better understood with reference to the appended drawings in which:

FIG. 5 is a perspective view of a formulation chamber, in the form of a drip chamber, usable according to the invention with a tabletted beneficial agent in non-controlled release dosage form in the shape of a substantially rectangular solid with slightly rounded corners disposed within the drip chamber, the beveled inlet tube end of the drip chamber being the upper end that is thrust in the normal manner through the closure of the supply container to communicate therewith and receive liquid enteral nutritional product therefrom;

FIG. 6 is a perspective view of the drip chamber of FIG. 5 inverted to show more of the detail of construction;

FIG. 7 is a perspective view of a suitable formulation chamber similar to that shown in FIG. 5 but with a different form of attachment for connection to a supply container, the screw cap here into which a supply container threadably fits being integrally formed with the closure or plug that fits into the inlet end of the body of the formulation chamber;

FIG. 8 is a perspective view of the formulation chamber shown in FIG. 7 as viewed in the opposite direction;

DEFINITIONS USED HEREIN

Figure 1:
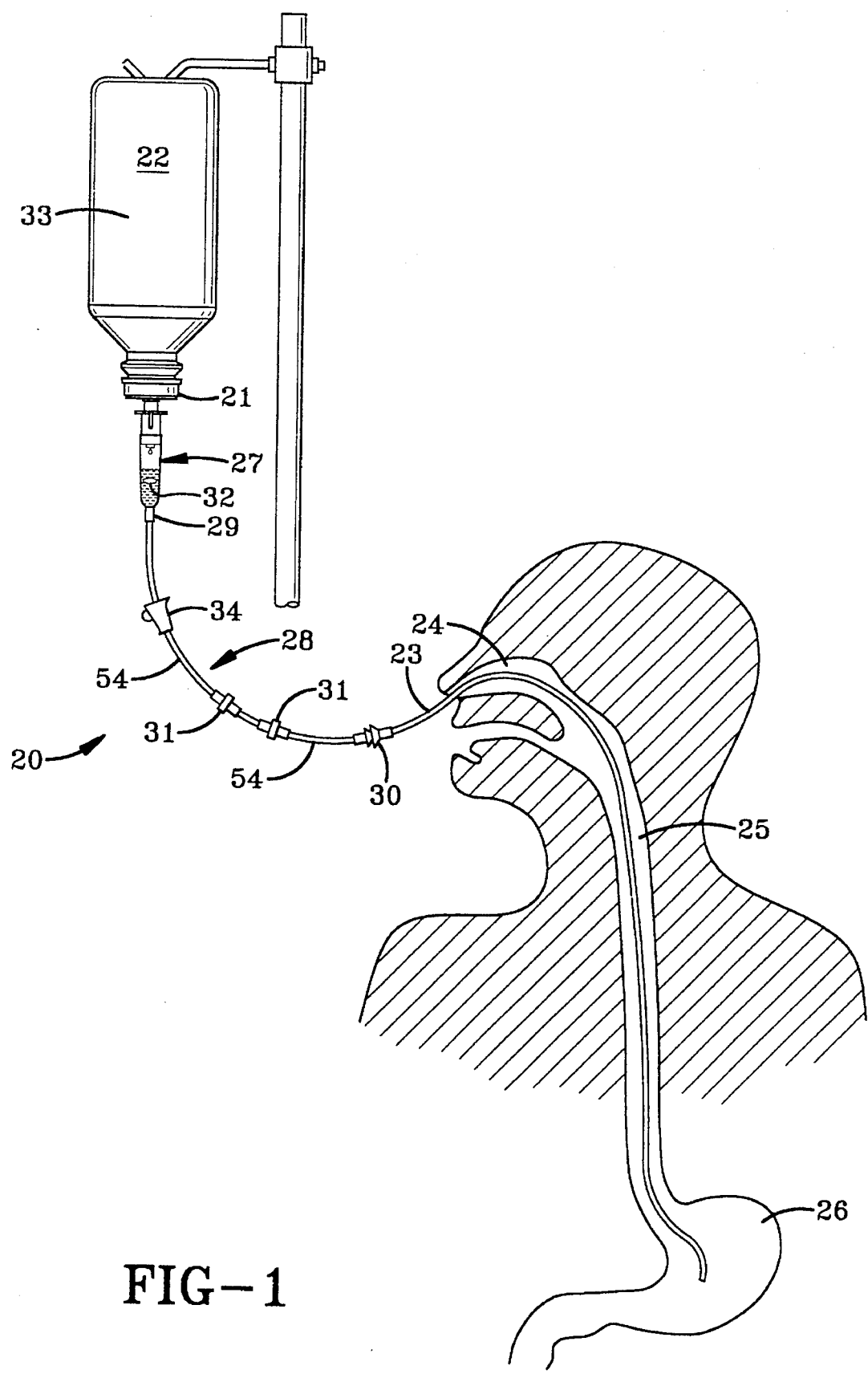
FIG. 1 is a partly schematic representation of an apparatus for modification of a liquid enteral nutritional product and tube feeding it nasogastrically according to the invention.

The following terms and phrases are defined for the purposes of the description and claims.

"Enteral" nutritional products refers to liquid compositions commonly understood to be supplied to and utilized in the gastrointestinal tracts of patients. Such enteral nutritional products have a viscosity in the range of 1 to about 300 cps. and most frequently in the range of about 5 to about 150 cps.

"Enteral nutritional product medium" refers to the liquid portion of a liquid enteral nutritional product, mainly water, but often including lesser or minor amounts of one or more liquid non-aqueous substances such as lipids, e.g., vegetable oil or marine oil.

The term "gastrointestinal tract" as used herein refers only to the stomach and the small bowel. Feeding to the gastrointestinal tract is done by use of a nasogastric tube extending through a nasal passage and the esophagus and thence to the stomach, or by use of a feeding tube extending through the abdominal wall to the stomach or small intestine.

A "physiologically significant" or "beneficial" agent is an ingredient that is, or is believed to be, nutritionally or pharmaceutically important to the patient, or is otherwise medically important as in the case of a probiotic, or, a diagnostic agent such as an opaquing agent.

A "probiotic" is understood to be a live microbial food supplement which beneficially affects the human host by improving the individual's microbial balance in the gastrointestinal tract, e.g., *Lactobacillus reuteri*.

A "beneficial agent or ingredient that is dispersible in the medium of the liquid enteral nutritional product" is an agent or ingredient that is physiologically beneficially added, or otherwise usefully beneficially added, as in the case of a diagnostic agent, to the liquid nutritional product during enteral feeding. The beneficial agent(s) or ingredient(s) taken up by the liquid enteral nutritional product in the formulation chamber according to the invention are not in controlled or sustained release dosage form and must be dispersible in the medium of the liquid enteral nutritional product being modified during feeding, in order to be carried along with the nutritional product into the gastrointestinal tract of the patient.

The term "dispersible" as used herein with respect to beneficial agent(s) or ingredient(s) is to be understood to apply to substances that are soluble as well as those that are suspendable enough to be taken up readily and carried along by the liquid medium as the liquid enteral nutritional product flows through the formulation chamber containing the one or more beneficial agents in non-controlled release dosage form plus any marker dye employed.

A "useful amount" of a beneficial agent that is dispersible in the medium of the liquid enteral nutritional product is an amount or quantity that is "physiologically effective" and is demonstrably so or reasonably expected to be physiologically effective with respect to a patient, i.e., in producing a detectable beneficial effect on the patient on either a short term or long term basis when fed as part of a liquid enteral nutritional product, or, is "diagnostically detectable", and is detectable in diagnosing a condition or disease.

The phrase "at least one beneficial agent dispersible in the medium of the liquid enteral nutritional product" is meant to refer to the singular as well as the plural, as may well be adjudged from the context, and includes combinations of ingredients, agents or factors.

The term "feeding set" refers to the combination of a drip chamber or other formulation chamber loaded with at least a useful amount of at least one beneficial agent as above defined and not in controlled release dosage form, along with, or without, a marker dye in controlled release form, and, fluid communication means connectable to a feeding tube for enteral feeding. The term "feeding set" also applies to the combination of a formulation chamber and a fluid communication means when supplied together, usually in the same package, with a useful quantity of at least one beneficial agent. The term also encompasses such a feeding set having at least one additional formulation chamber in fluid flow series or connectable in parallel to separate supply containers, as a part of the fluid communication means. None of the formulation chambers in the foregoing sets described contains or is accompanied by a beneficial agent, as above defined, in controlled release dosage form.

The term "a controlled release dosage form" refers to any of the well known conventional controlled release dosage forms, such as, a coated tablet, osmotic delivery device, coated capsule, microencapsulated microspheres, coated agglomerated particles, e.g., as of molecular sieve particles, or a permeable fine fiber bundle, that contains and stores and subsequently releases an ingredient content of beneficial agent into the medium of a liquid nutritional product at room temperature in a retarded, or delayed or intermittent manner as compared to the solubility characteristics normally exhibited by the uncoated particulate beneficial agent in the said medium at about room temperature. Any dosage form which employs coating, encapsulation, microencapsulation, enclosure in an osmotically driven device, or capture in a molecular sieving type structure or in a permeable fine hollow fiber, to retard or slow down, delay or intermittently delay solubilization of a promptly soluble beneficial agent so that its dissolution, or dispersion as with an osmotically driven device, takes place over at least a 30 minute time period and preferably over at least a two hour time period, is exhibiting a sustained release form of controlled release. As to a beneficial agent that is inherently not promptly soluble in the medium of a nutritional product, any such dosage forms that retard or slow down, delay or intermittently delay solubilization of such a beneficial agent by at least 20 percent of the normal time for solubilization or dispersion into the medium of a liquid enteral nutritional product, of a given unit amount of the beneficial agent that is not coated or treated to obtain a controlled release, is considered for the purpose of the description and claims to be a controlled release dosage form.

On the other hand merely tableting a beneficial agent either unmixed with another material, or not admixed with a relatively insoluble binder type excipient, for example, while resulting in a smaller surface area being exposed to a solvent liquid and a slower dissolution rate than that of a fine particulate form, is not to be considered in controlled release dosage form. Clearly, a beneficial agent in a particulate form that has not been coated with or enclosed in any other material is not in controlled release dosage form. Nor are uncoated tablets or particles of a beneficial agent, clearly not in controlled release dosage form, to be considered transformed into controlled release dosage form merely by being enclosed in a carrier such as a fibrous tea bag type of packet or an easily dissolved or disintegrated capsule, such as a very thin gelatin capsule.

The term "controlled release" is intended to embrace sustained release as well as intermittent and delayed release.

The beneficial agents used solely according to the invention are not in "controlled release dosage form" as defined above. The marker dye or dye mixtures employed, however, are in controlled release dosage form which is understood to include delayed or intermittent release as well as sustained release dosage forms. It should also be understood that the phrase "flowing the liquid enteral nutritional product through the apparatus, wherein it becomes modified, and into the feeding tube" is meant to include utilizing gravity flow from a hanging container, as well as using a pump in addition to or without gravity flow to promote the flow of the modified enteral nutritional product into and through a feeding tube.

DETAILED DESCRIPTION OF THE INVENTION

Referring now to the drawings in which like parts are referred to by like reference numerals, the apparatus of the invention is shown in FIG. 1 in the form of a feeding set, indicated generally by the numeral 20, connecting the outlet 21 of the hanging supply container 22 to the nasogastric feeding tube 23 that extends through a nasal passage 24 of the patient and down the esophagus 25 to the stomach 26. The feeding set here consists of a formulation chamber 27, in the form of a drip chamber that serves also as a formulation or contact chamber, and fluid communication means indicated generally by the numeral 28.

Figure 3:
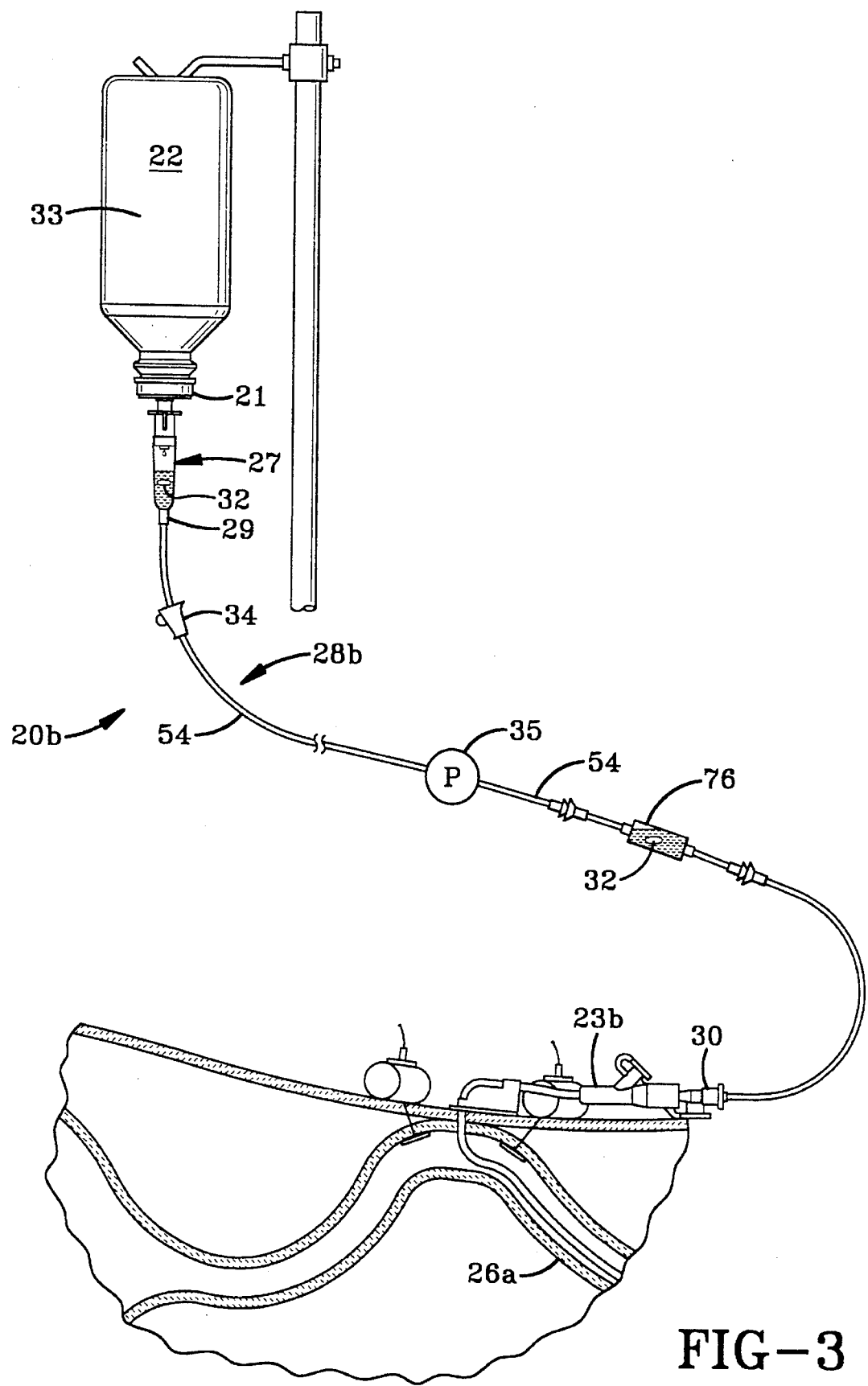
FIG. 3 is a partly schematic representation of an apparatus for modification of a liquid enteral nutritional product and tube feeding it, with the aid of a pump, via a jejunostomy tube according to the invention.
Figure 16:
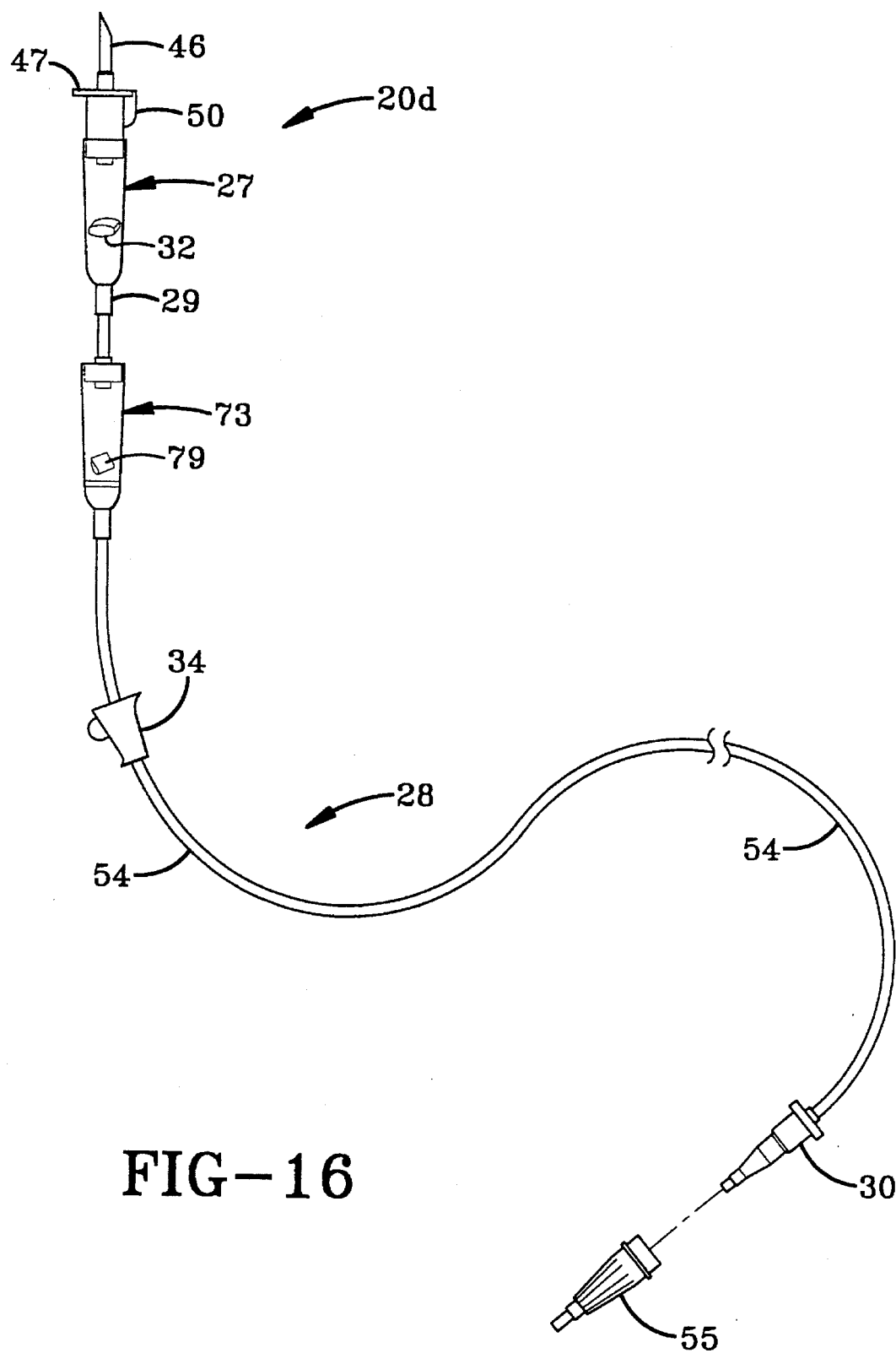
FIG. 16 is a view in side elevation of a feeding set similar to that of FIG. 14 but in which two formulation chambers in the form of drip chambers are connected in tandem.
Figure 17:
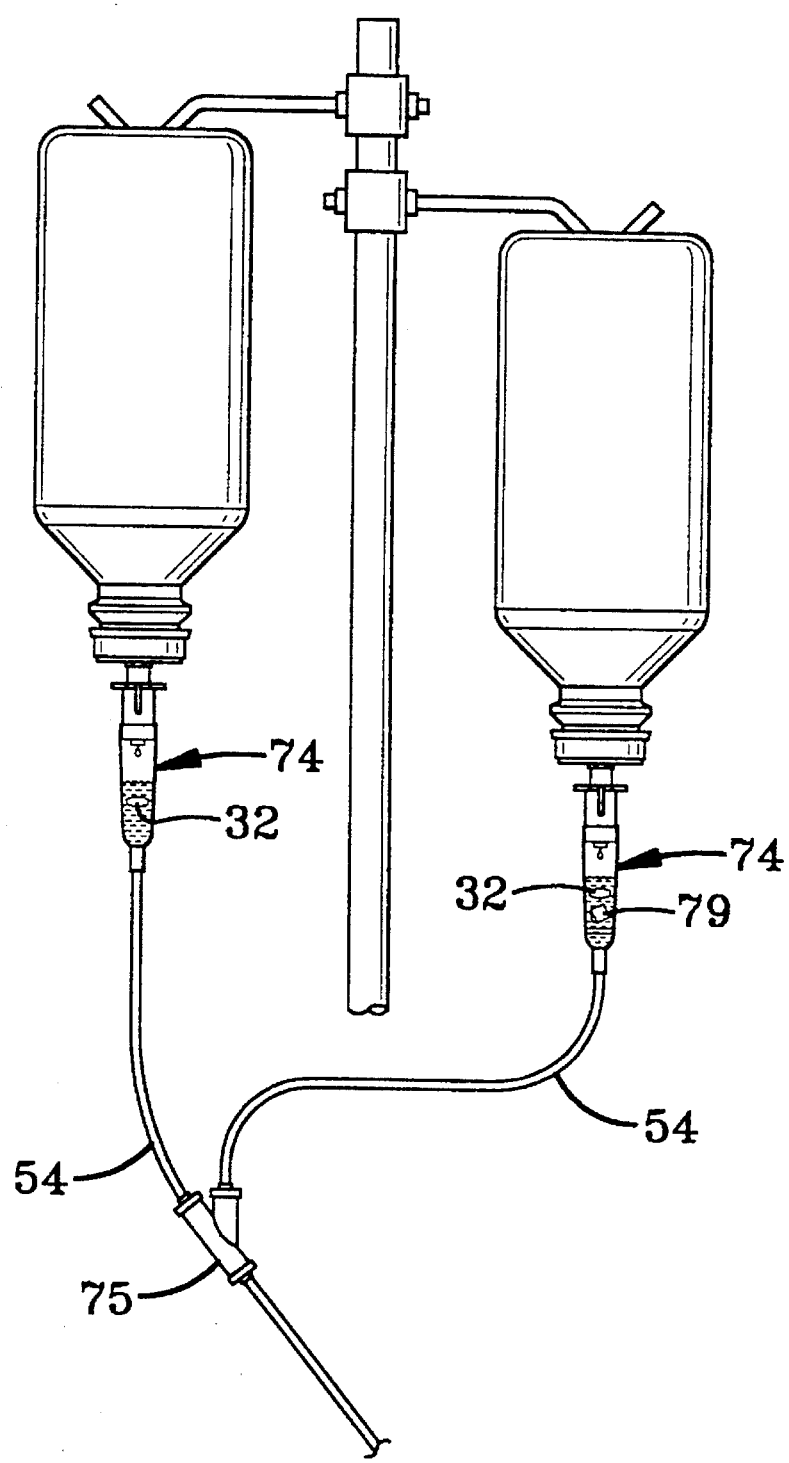
FIG. 17 is a view in side elevation of part of the apparatus for modifying a liquid enteral nutritional product during enteral feeding wherein two formulation chambers are suspended from respective hanging supply containers, each containing liquid enteral nutritional product, the outlets of the formulation chambers being connected to tubing segments that connect to a "Y" fitting that joins the parallel flow from each formulation chamber into a single stream within the communication means, here truncated.

"Fluid communication means" is to be understood to include all components of fluid communication utilized in series from the formulation chamber outlet 29 to the connection 30 to the feeding tube, such as the nasogastric feeding tube 23. Components include not only portions of flexible tubing 54 but also any additional drip chambers or other formulation chambers connected in series as seen in FIGS. 3 and 16 for series flow, or in parallel but soon joined into a single stream as seen in FIG. 17, for flow of the liquid enteral nutritional product to the feeding tube of the patient. The components may also include any special tubing portions needed for utilization of a pump, and, connector elements, respectively, between all the other components, such as connector elements 31 or adapters 30.

It may be helpful to utilize two formulation chambers in tandem, such as drip chambers 27 and 73 as seen in FIG. 16, to introduce a greater concentration or amount of a given ingredient. The formulation chambers may be used in tandem also to introduce different respective ingredients that are not supplied together within the same pre-filled or pre-loaded formulation chamber. They may constitute a little-used combination, for example, or a combination that is not compatible in storage together in admixture or close proximity within a pre-filled formulation chamber.

As indicated above, two formulation chambers are shown in use sequentially in feeding sets in FIGS. 3 and 16. In the set shown as part of the apparatus of FIG. 3, the second formulation chamber 76 is attached near the end of the flexible tubing 54 which is distal from the supply container 22. This may be found useful for adding a special ingredient to a feeding set already made up. With the formulation chamber 76 near the end of the set which is distal from the supply container, it will most likely be positioned approximately horizontal and care must be taken to assure good contact of the flowing liquid enteral nutritional product with the beneficial agent content of this second formulation chamber. If desired, this second formulation chamber may be shaped with a depression or pocket or a channel in which to position the beneficial agent content and through which the nutritional product will flow.

Dual formulation chambers 74 may be used in parallel depending from dual supply containers, as indicated in FIG. 17, and for similar reasons as the tandem chambers, or, it may be simpler wherein it is desired to administer one beneficial agent completely before starting to administer another. It is preferable to hang such supply containers, as shown, to avoid problems of control in order to get adequate flow through both formulation chambers from a single supply container. The outlets of each formulation chamber shown in FIG. 17 are connected to segments of flexible tubing 54 that lead to a "Y" fitting 75 in which the streams of liquid enteral nutritional product are joined to be conducted as a single stream to a feeding tube.

Referring again to FIG. 1, the formulation chamber 27 has positioned therein a useful quantity or dose 32 of one or more beneficial agents none of which are in controlled release dosage form, in addition to one or more marker dyes in controlled release dosage form, if included. The useful quantity or dose 32 constitutes at least a physiologically effective or diagnostically detectable amount of at least one beneficial agent that is dispersible in the medium of the liquid enteral nutritional product 33 flowing from the supply container 22 into the formulation chamber 27 where the liquid enteral nutritional product 33, which is normally water-based, contacts the dose 32 of one or more beneficial agents and any marker dye within the formulation chamber 27, causing their uptake into the flowing liquid enteral nutritional product. The flow of liquid enteral nutritional product is conveniently started or shut off or sometimes regulated by the use of a conventional adjustable compression clip 34.

Figure 2:
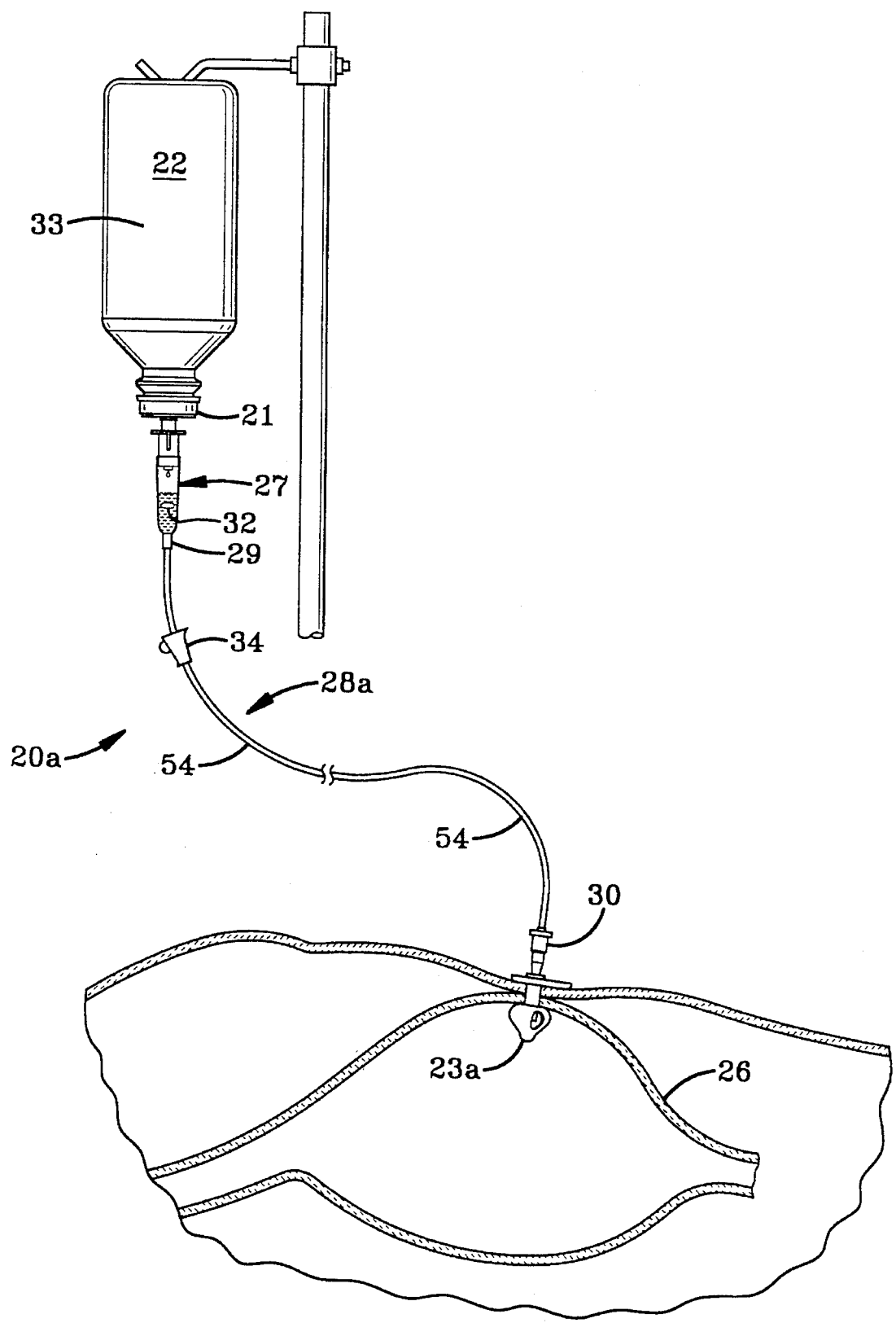
FIG. 2 is a partly schematic representation of an apparatus for modification of a liquid enteral nutritional product and tube feeding it via a gastrostomy tube according to the invention.

Turning now to FIG. 2, a hanging supply container 22 is shown supplying liquid enteral nutritional product 33 to a formulation chamber 27 from which the liquid enteral nutritional product flows through flexible tubing 54 of the feeding set 20a to the gastrostomy feeding tube 23a. The gastrostomy feeding tube shown in FIG. 2 is merely exemplary of the large variety of gastrostomy feeding tubes which are commercially available, it being understood that the apparatus of the invention is usable with a variety of gastrostomy or other ostomy tubes.

In FIG. 3 there is shown a feeding arrangement for a jejunostomy much like the apparatus in FIG. 1, except that feeding set 20b is adapted to be used with a pump 35, which provides positive flow into a feeding tube 23b leading to the small bowel 26a of the patient, whereas in a number of cases gravity flow is utilized. Also, a second formulation chamber 76 is employed as part of the feeding set 20b in order to add additional or different beneficial agent and/or marker dye, each dispersible in the medium of the liquid enteral nutritional product 33 flowing from the hanging supply container 22 to formulation chamber 27 of feeding set 20b and thence through the rest of the communication means 28b of feeding set 20b and second formulation chamber 76 to the jejunostomy feeding tube 23b.

If desired, or needed, as often is the case when feeding via a feeding tube, such as a jejunostomy tube, a pump 35, such as a peristaltic pump with cam action acting upon the flexible tube portion 54 of the communication means 28b, or a positive displacement pump with a disposable fluid infusion pumping chamber cassette such as that described in U.S. Pat. 4,927,411, and connected in series in the communication means, may be used to flow or help flow the modified liquid enteral nutritional product into the feeding tube, for example, when it is not convenient to hang or otherwise locate the supply container in an elevated position relative to the patient, or, when the nutritional product is rather viscous and flows slowly by gravity flow. The fluid communication means, such as means 28b, of the apparatus utilized will ordinarily include a flexible tube portion 54 connectable to or usable with a conventional pump. If the pump employed, for example, is a peristaltic pump which requires the use of tubing with a specially shaped portion, such tubing may be substituted for all or a part of the communication means delivering modified liquid enteral nutritional product to the feeding tube of the patient.

Figure 14:
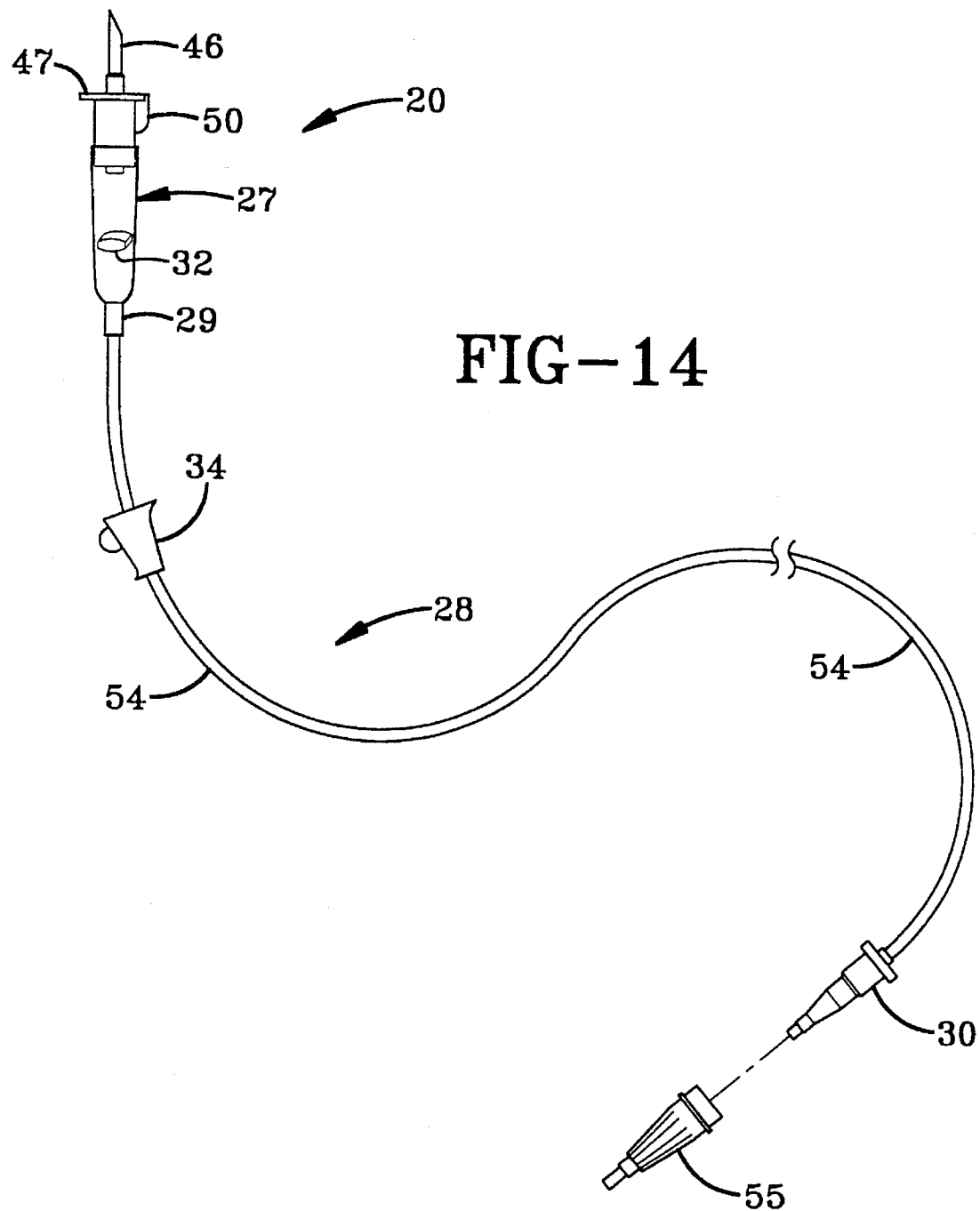
FIG. 14 is a view in side elevation of a feeding set that is useful as a kit according to the invention, the set including a drip chamber as the formulation chamber with one or more beneficial agents in a compressed but uncoated tablet in the formulation chamber, and fluid communication means attached to the outlet of the formulation chamber, the fluid communication means having a protective removable cap over the end connector which is adapted to be connected to a conventional feeding tube, and the fluid communication means being broken and foreshortened for purposes of illustration.
Figure 15:
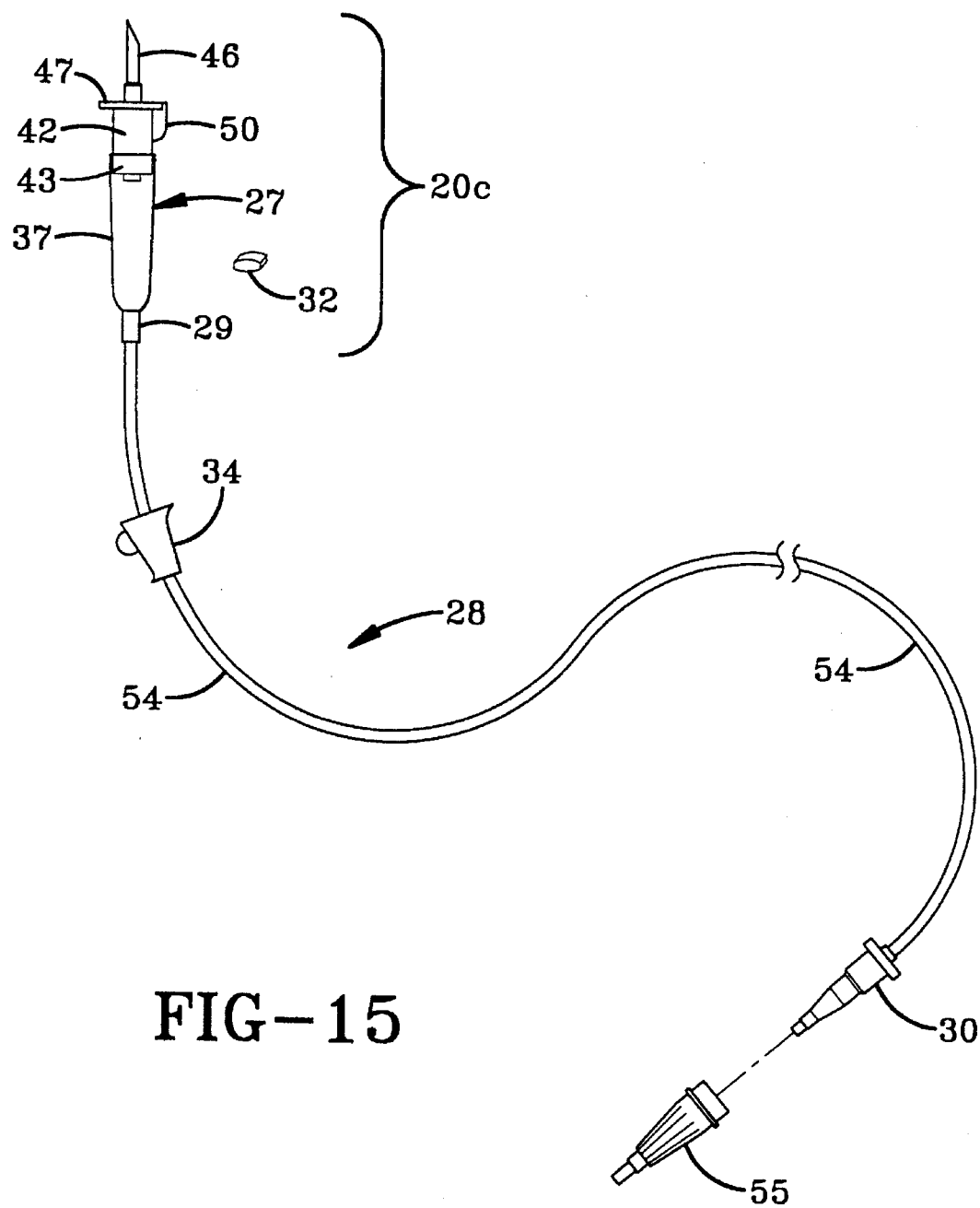
FIG. 15 is a view in side elevation of a feeding set, or kit, much like that shown in FIG. 14, except that the compressed uncoated tablet containing one or more beneficial agents has not been placed in the drip chamber, but accompanies the drip chamber and attached fluid communication means.

The end of the flexible tubing 54 connecting to the inlet end of second formulation chamber 76 is preferably provided with a coupling element 30 such as that shown in the feeding sets in FIGS. 14–16, while the inlet end of the formulation chamber 76 is preferably shaped complementarily to receive the coupling element 30, and the outlet of the formulation chamber 76 communicates with a short length of flexible tubing which likewise terminates in a coupling element 30, that is connected to the feeding tube 23b. It may be seen that it is convenient to add the second formulation chamber 76, when the need arises, without having to disconnect the parts of the feeding set. Here, for example, the flexible tubing 54 would have to be disconnected from the formulation chamber 27 to add the formulation chamber 76 immediately adjacent thereto.

The formulation chamber 76 may be hung vertically, like a conventional drip chamber, but will generally be positioned with the direction of flow of the liquid nutritional product therethrough approximately horizontal. Consequently, the formulation chamber 76 should be provided with means to guide or channel the flowing liquid enteral nutritional product over the dose 32 of beneficial agent and any marker dye dosage forms therein. Such means may be a low lying co-axial channel or a bulbous enlargement of the chamber body or even a lateral depression in the sidewall of the lower side of the chamber, or, a trap, or weir, or any other means to retain the dose 32 of one or more beneficial agents and any marker dye where there will be an adequate flow or depth of liquid sufficient to afford good contact with the beneficial agents and dye located in such guide or channel means.

Figure 4:
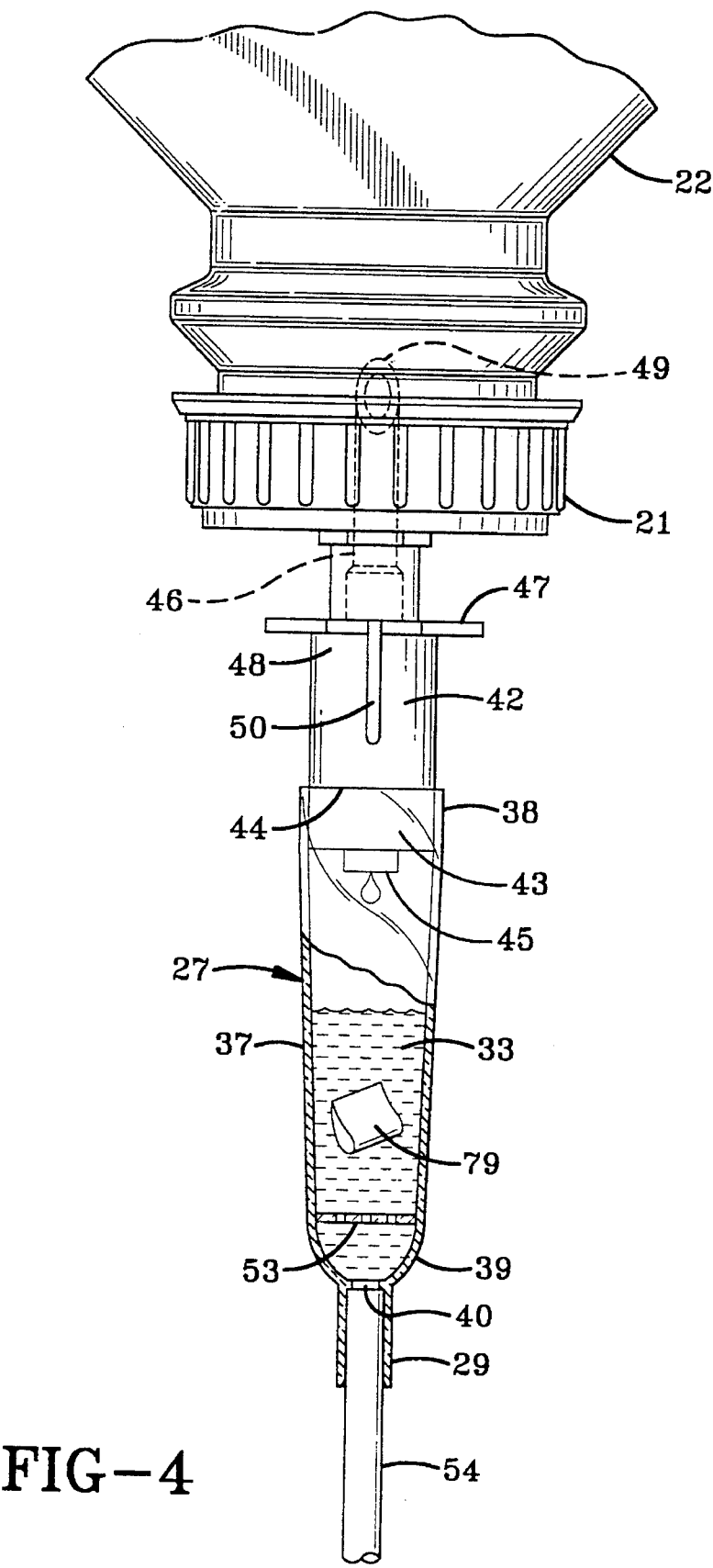
FIG. 4 is an enlarged fragmentary view in front elevation of the lower portion of a hanging supply container of a liquid enteral nutritional product, such as the container shown in FIGS. 1 to 3, with the beveled inlet tube of a drip chamber inserted through the closure and depending therefrom and with a beneficial agent in loose particulate form within a fibrous tea bag-like envelope and disposed inside the drip chamber and immersed in the flowing liquid enteral nutritional product, the lower part of the drip chamber being partly broken away and in section, and the tubing portion of the fluid communication means, i.e., primarily the tubing leading away from the drip chamber, being truncated for purposes of illustration.

In the enlarged fragmentary view in FIG. 4, a fibrous packet 79 containing a dose of beneficial agent (not visible) is seen immersed in liquid enteral nutritional product 33 within the formulation chamber 27. The dose in the fibrous packet 79 in FIG. 4 is not in controlled release form but in the form of loose particles or tablets. The dose of beneficial agent may be in the form of particles or tablets of a wide range of sizes or dimensions, but free of any coating or other controlled release mechanism other than the size of the particles or tablets that would inhibit disintegration and dissolution, so long as the dose normally dissolves or disintegrates in the flow of liquid enteral nutritional product in less than two hours and in many instances less than about 30 minutes. The form of the dose is preferably, in quantity, a kind of unit, such as a tablet, or an agglomerate, or a filled but easily dissolved or disintegrated capsule, or, a measured quantity of loose particulate material held, for example, in a highly permeable carrier, such as a porous fibrous tea bag type envelope. Individual tablets or other particles, or, capsules, should have a geometric shape, for example, of that of a rectangular solid or a somewhat pointed star shape, that will avoid blocking or hindering flow of liquid enteral nutritional product 33 out of the outlet orifice 40 of the formulation chamber 27, or, other means such as a mesh sleeve may be employed to support a dose 32, or a plurality of doses 32, to prevent blockage. Wherein one or more marker dyes in controlled release dosage form is employed along with beneficial agent it is important to likewise similarly avoid blockage of the outlet orifice 40 by the controlled release dosage form of the marker dye or dyes.

An easily disintegrated or dissolved capsule for use in holding a quantity or dose of beneficial agent may be formed of, for example, a thin-walled water soluble gelatin material.

The details of construction of a conventional drip chamber are illustrated in FIGS. 5 and 6, which are greatly enlarged perspective views. The drip chamber 27 as shown has two parts. The first part is a hollow, nearly cylindrical chamber body 37 with an open upper inlet end 38 and a lower outlet end 39 that tapers or narrows down to form an orifice 40 leading to an integrally formed outlet tube portion 29. The chamber body 37 must be formed of a clear material, such as glass or clear plastic, to allow see-through visibility of the flow of the nutritional product. Usually the drip chamber is formed of a clear, somewhat flexible, autoclaveable plastic, such as a clear polyvinylchloride or polyolefin resin.

The second part of the drip chamber 27 shown is in the nature of a plug 42 with a cylindrical body that has an inward end portion 43 that snugly press fits into the upper, i.e., inlet, end 38 of the chamber body 37. Preferably the end portion 43 of the plug body 37 that extends into the chamber body has a slightly reduced diameter. The edge 44, of this end portion 43, remote from the end face of the plug, is raised slightly, being a little larger in diameter, and serves as a stop when assembling the chamber body and the plug together. The plug body is provided with an integrally formed fluid communication passage 45 which may take the form of an axial borehole in a solid plug body that communicates with an inlet tube portion 46 that projects outwardly in the axial direction from a collar-like flange 47 that extends radially from the top end 48 of the plug body. But, preferably, in order to provide a plug body with more resiliency for easier insertion into the upper inlet end 38 of the chamber body 37, the fluid communication passage 45 is a concentric tube axially located within and about as long as the plug body. The concentric tube 45 is integrally formed with or otherwise operatively connected to the inlet tube portion 46. A short, peripheral, integrally formed flange 50 that extends longitudinally from the collar-like flange 47 along a side of the plug body may be provided, if desired, to aid in gripping the plug body when assembling the drip chamber.

The plug may be molded of a plastic such as a polyvinylchloride resin, which may be pigmented, if desired, for visibility as an aid to observe proper seating.

The distal or free end 49 of the inlet tube portion 46 has a sufficiently sharp beveled end to facilitate puncturing the seal (not shown) in the closure in the neck of the conventional hanging supply container, such as supply container 22. The collar-like flange 47 may serve as a stop to the insertion of the pointed inlet tube portion 46 into the closure at the neck of the supply container 22.

Other modes of construction of the drip chamber may be employed so long as a suitable connection to the supply container is provided as well as a see-through tubular portion wherein the rate of flow of the liquid enteral nutritional product may be observed. For example, see the formulation chamber 82 depicted in FIGS. 7 and 8 wherein the plug end 83 of the formulation chamber is integrally formed with the closure 84 for a conventional supply container to be threadably connected thereto. The apparatus of the invention is not to be considered limited to the inclusion of the drip chambers here used by way of illustration, nor is the method limited to the use thereof.

The drip chamber shown in FIGS. 5 and 6 has one or more beneficial agents as dose 32 in uncoated tablet form disposed therein ready for use. The one or more doses 32 will be preselected according to the contents thereof to provide the supplemental additional nutrient(s) and/or medicament(s) and/or other beneficial agent(s) selected by the caregiver in charge, along with a marker dye, if desired. As used herein, and in the claims, medicaments are understood to be substances used in therapy.

More than one dose 32 of beneficial agents may be placed in the formulation chamber as desired to provide a combination selected from nutrients or medicaments or other beneficial agents tailored to the needs of the patient being fed. For example, a nutrient such as glutamine and one of the probiotics might be added as a supplement to a liquid enteral nutritional product, or either or both of these together with a medicament to be added to a liquid enteral nutritional product. Generally the nutrients added in the formulation chamber according to the invention will be those that are suitable to add as a bolus feeding, while other types of beneficial agents added in this manner, such as medicaments, will be those that need to be, or may be, added over a short time period, such as about thirty minutes or less, and clearly in less than two hours.

As indicated, the dose 32 of beneficial agent will usually be in the form of one or more tablets, particles in one or more capsules, one or more agglomerates of particles, or loose particles in one or more carriers, such as a porous fibrous carrier like a non-woven tea bag. It is highly desirable to avoid having the dose or doses 32 in whatever physical form block or greatly hinder the flow of the enteral nutritional composition out the orifice 40 of the outlet 29 of a formulation chamber, such as formulation chamber 27. If a dose 32 takes the solid rigid form of a tablet or capsule or agglomerate particle, it is preferred that the rigid form have a geometric shape, e.g., a polyhedron such as a rectangular solid, or, a star shape, any of which will not block a round passageway. A dose 32 in tablet form in the shape of a rectangular solid is shown in the formulation chamber depicted in FIGS. 5 and 6 as well as FIGS. 7 and 8.

Figure 11:
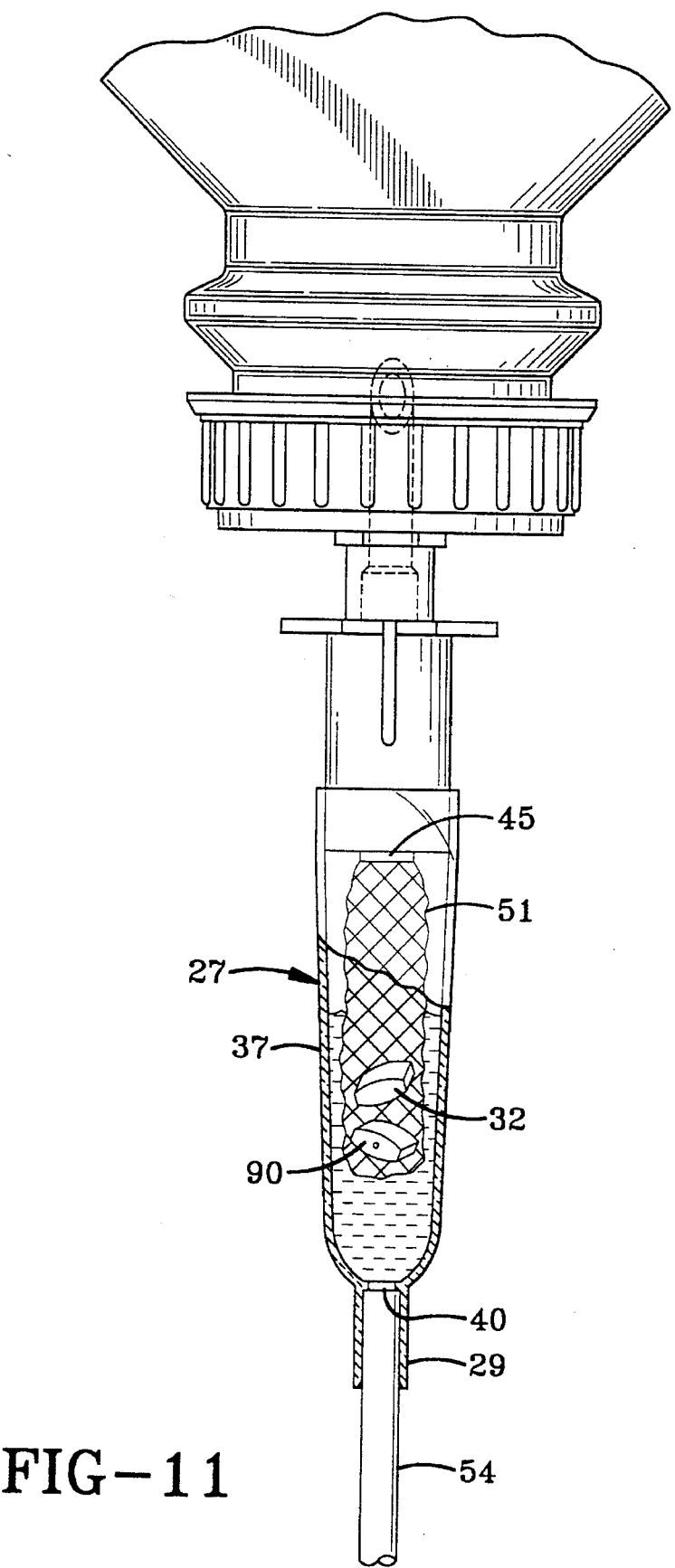
FIG. 11 is a view similar to FIG. 4, but with the beneficial agent in tablet or capsule form together with a marker dye in controlled release dosage form confined and supported within a mesh sleeve or bag.
Figure 12:
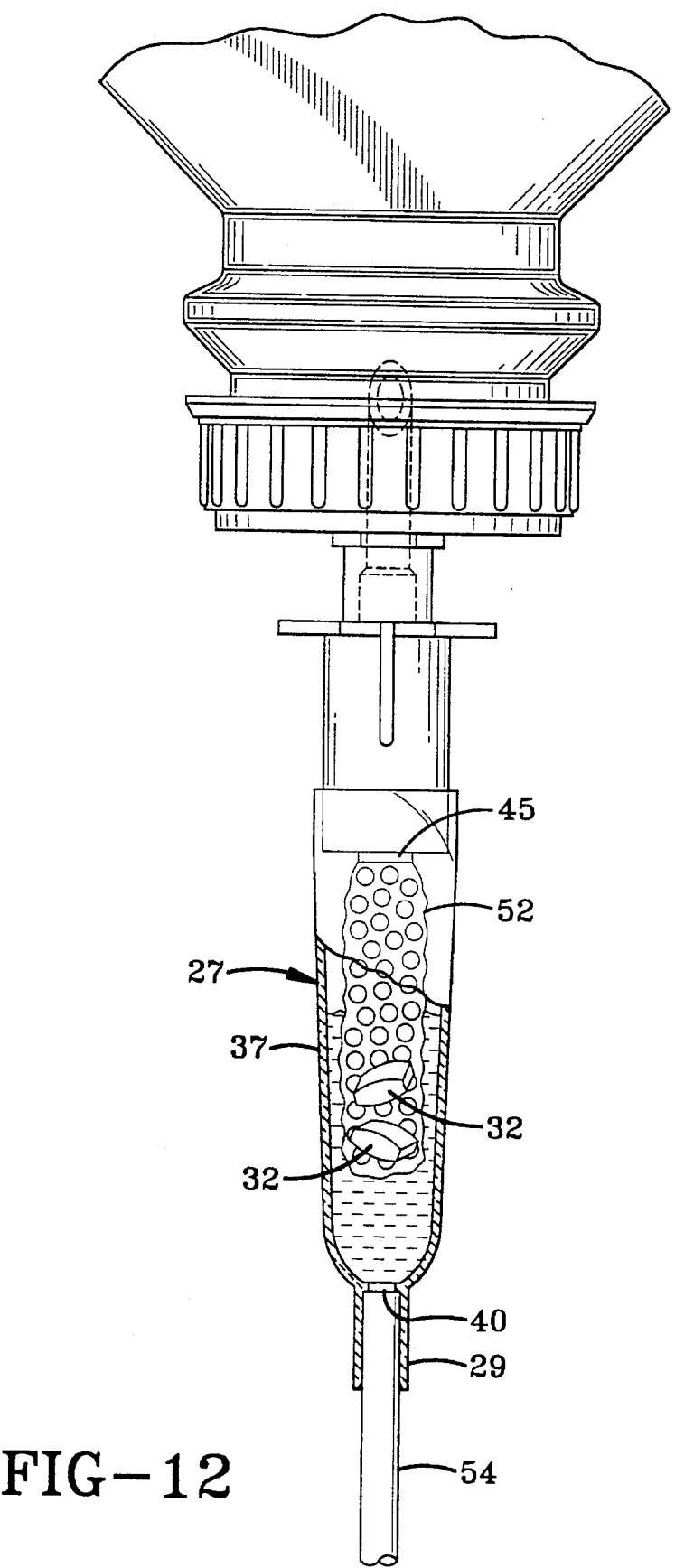
FIG. 12 is a view similar to FIG. 4, but with some beneficial agent in uncoated tablet form confined within a foraminated, or pierced, sleeve or bag.
Figures 13, 13A:
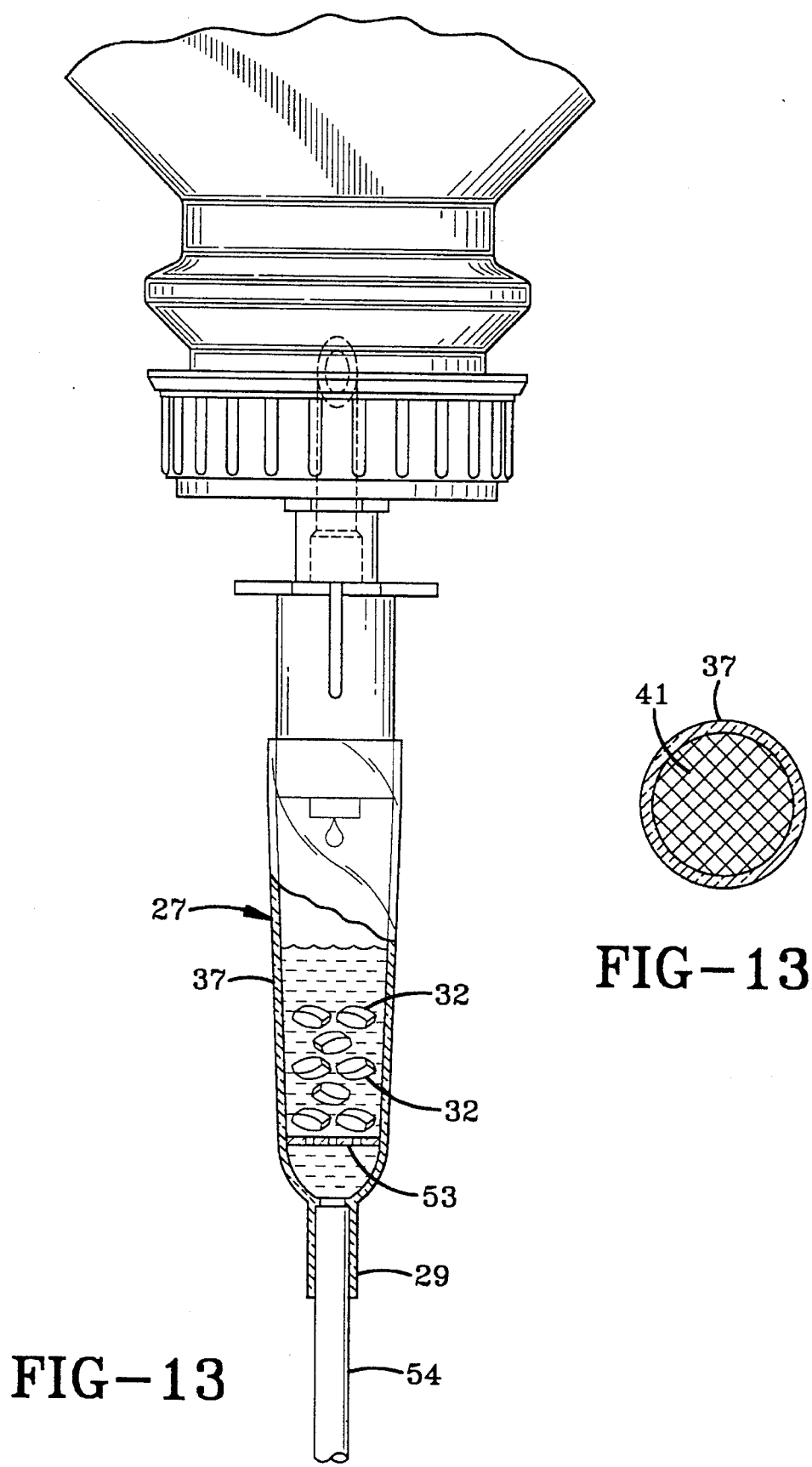
FIG. 13 is a view similar to FIG. 4, but with the beneficial agent as uncoated tablets supported by a foraminous plate above the bottom orifice of the formulation chamber.
FIG. 13A is a view in transverse section of a formulation chamber taken at a level just above a grid that has been placed in the formulation chamber of FIG. 13 in place of the foraminous plate there shown for the support of uncoated tablets of beneficial agent, and any marker dye employed in sustained release dosage form, positioned in the formulation chamber.

Blocking of the outlet of a formulation chamber may also be avoided by confining the solid shapes in a sleeve or bag supported within a formulation chamber, e.g., from the inlet tube thereof. In FIG. 11 a dosage form of a tabletted beneficial agent and a marker dye in an osmotically driven controlled release dosage form are shown confined in a mesh bag supported from the inlet tube 45. In FIG. 12 there is shown two doses 32 of beneficial agent in tablet form confined together within a foraminous bag supported from the inlet tube 45. In FIG. 13 there are shown doses 32 of beneficial agent in tabletted form supported on a pierced or foraminous plate 53. The plate 53 may be made of ceramic or rigid plastic material or inert metal such as stainless steel and disposed transversely across the chamber body 37 just above the outlet orifice 40. A grid such as that shown in FIG. 13A may be used instead of a plate as a support within the formulation chamber for doses 32 of beneficial agent. The grid may also be made of inert material such as a ceramic or rigid plastic material or inert metal.

Figure 9:
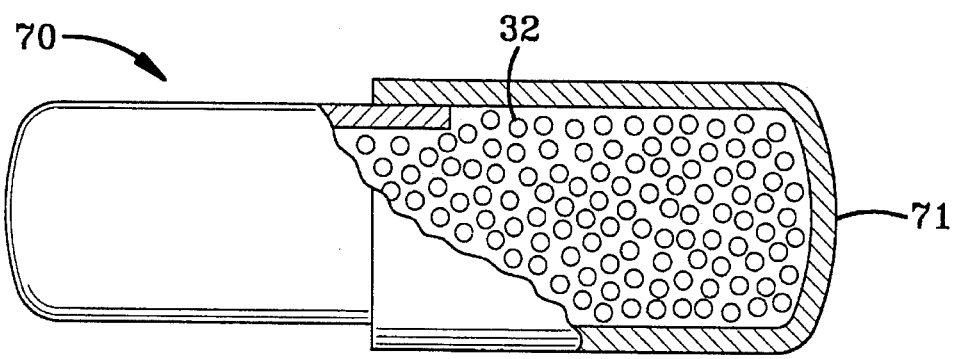
FIG. 9 is view in side elevation and partly broken away and in section of an easily soluble or disintegrable capsule-type carrier containing beneficial agent in particulate form and not in controlled release dosage form.
Figures 10, 10A:
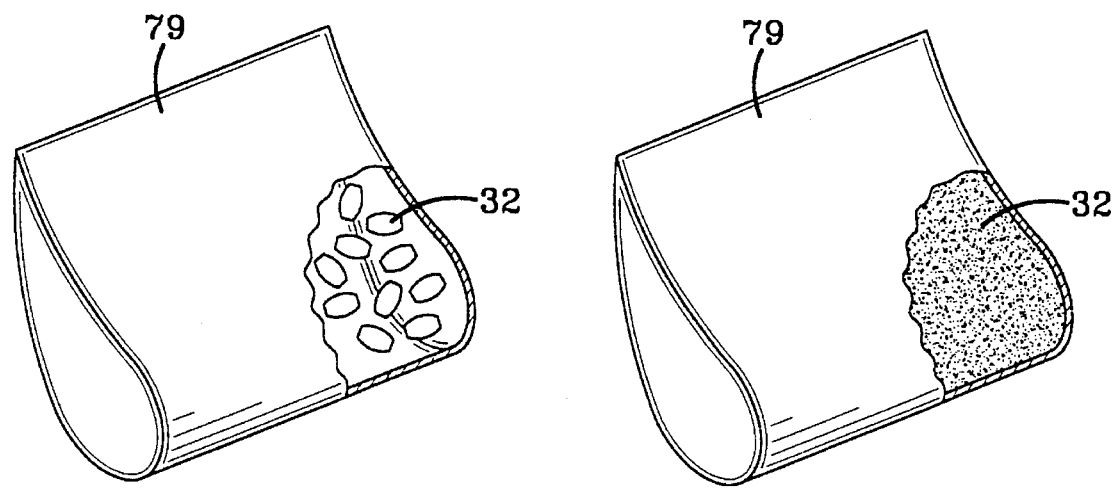
FIG. 10 is a perspective view, partly broken away and in section, of a highly permeable fibrous packet, preferably of the non-woven tea bag-type of carrier, suitable for inserting into a drip chamber, or other formulation chamber, and capable of holding a quantity of beneficial agent not in controlled release dosage form, e.g., in tabletted form or in an easily soluble or disintegrable capsule.
FIG. 10A is a perspective view partly broken away and in section of a fibrous packet similar to that seen in FIG. 10, but with the fibrous packet containing a quantity of one or more beneficial agents in loose particulate form.

If the physical form of any of the doses 32 is simply loose particulate, it is preferred to confine the particles in a dosage quantity in a carrier such as a porous or quickly disintegrating capsule or an envelope of the tea bag type. In FIG. 9 a capsule 70 is seen to have telescoping cap sections formed of a material that is very porous or disintegrates quickly, such as a reconstituted cellulosic material, enclosing a dosage amount of particulate beneficial agent. In FIG. 10 there may be seen a porous, fibrous envelope 79, preferably non-woven, of the tea bag type enclosing a dosage amount or quantity 32 of a particulate beneficial agent or a mixture of beneficial agents in tablet form, while in FIG. 10A there is depicted a tea bag type carrier containing a dose of particulate beneficial agent. The capsule carrier may be preferred for longer term storage purposes, while the tea bag type may be preferred because of the easy permeability to the medium of the liquid enteral nutritional product in the formulation chamber. The foregoing means of confining, i.e., supporting, the doses 32 within the formulation chamber 27 may also be used in any additional formulation chambers in the feeding set employed.

Wherein a marker dye is employed along with one or more doses of beneficial agent or agents according to the invention, the marker dye is not only useful as a marker during the shorter term while beneficial agents not in controlled dosage form are dispersing into the liquid enteral nutritional product, but also during the remainder of the up to 24 hours or more during feeding of the quantity of liquid enteral nutritional product usually provided in the conventional supply container, i.e., up to about three liters. A marker dye, if a colorant dye visible under white light, i.e., daylight or the artificial light normally encountered in hospital settings, provides a visual indicator that the nutritional product is continuing to flow through the drip chamber form of formulation chamber. A marker dye also may be an important aid to detection of liquid enteral nutritional product that has refluxed from the stomach or small bowel of a patient for any of various reasons and may find its way into the lungs calling for special care to be given promptly.

A marker dye or dye mixture that is useful according to the invention when used in conjunction with a beneficial agent not in controlled release dosage form is a colorant dye, or a fluorescent dye, or a mixture of such dyes, that is physiologically acceptable to the patient and compatible with the beneficial agents being fed therewith. The dye or dye mixture must also be capable of being taken up in detectable concentration in the liquid medium of the liquid enteral nutritional product while the product flows through a drip chamber or other formulation chamber having the controlled dosage form of the dye or dye mixture positioned therein. If the dye is detectable in the drip chamber it can be expected to be detectable if it in some manner reaches the oral cavity of a patient.

The marker dye employed may be a colorant dye that imparts color that is visible under white light, for example, normal daylight or artificial room light encountered in a hospital or clinic, or, the marker dye may be a fluorescing dye that fluoresces visibly under ultraviolet light, or a mixture of a colorant dye and a fluorescing dye. A mixture of a colorant dye and a fluorescing dye may be especially advantageous in that the flow through the formulation chamber is readily perceived under normal lighting conditions with colorant dye present, while even a small amount of nutritional product out of place, for example, in the oral cavity or nasal passage, will be more easily detected with the aid of ultraviolet light if it contains a fluorescing dye. This is because of the nature of the fluorescing dyes that are especially visible under ultraviolet light even when present in very low concentration.

The dye or dye mixture used must be physiologically acceptable. Usually food grade colorant dyes approved under the provisions of the United States Food, Drug and Cosmetic Act are suitable. Preferred are F.D.& C. Blue #1 and F.D.& C. Blue #2 dyes. The dye or dye mixture must be soluble in the medium of the liquid enteral nutritional product being fed and compatible with the beneficial agent or agents being added during the feeding. Generally about 0.1 milligram (mg) of dye per milliliter of liquid enteral nutritional product is desired to give a readily visible coloration to the nutritional product.

Wherein it is important to be able to detect misdirected liquid enteral nutritional product, the marker dye used may be a fluorescing dye, such as F.D.& C. Red #3, which is highly visible at a very low concentration under ultraviolet light and also imparts a visible coloration to liquid enteral nutritional products under white light conditions. Other suitable fluorescing dyes are: quinine, F.D.& C. Red #22, F.D.& C. Red #28, fluorescein, and D 282 UV Blue available from DaGlo of Cincinnati, Ohio, and also identified as 16470-24-9 in the Chemical Abstracts System with a color index of 220 as a fluorescent brightener. As indicated above, if desired, a mixture of colorant dye and fluorescing dye may be used. Generally, adding to the nutritional product in the formulation chamber about 0.01 to 0.05 mg/ml of fluorescing dye is adequate for detectability under ultraviolet light.

Figure 18:
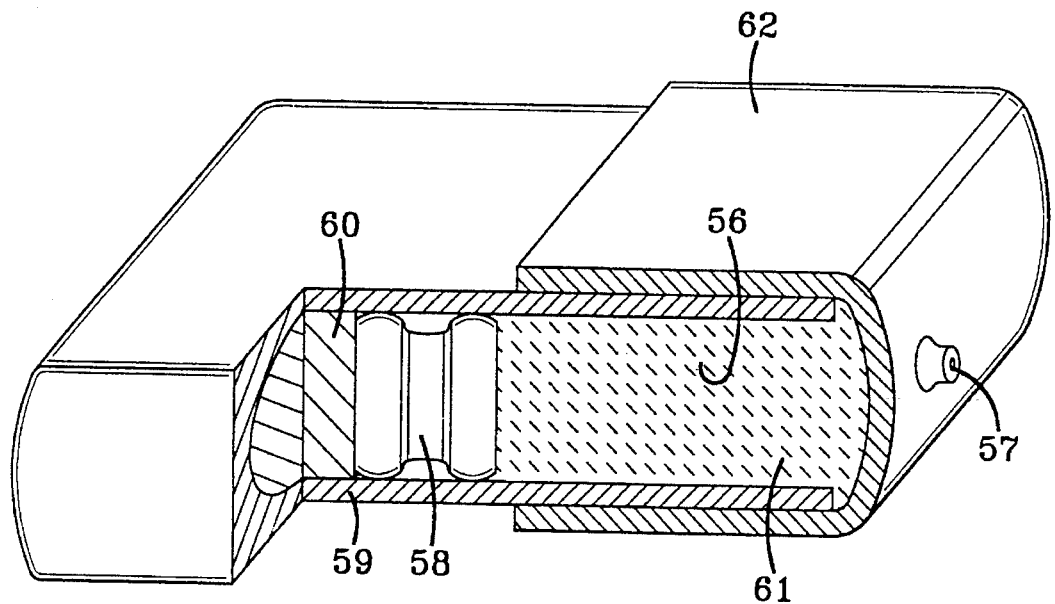
FIG. 18 is a view in side elevation and partly broken away and in section of a suitable form of osmotic delivery device for sustained release of a marker dye or dye mixture.

In order to provide a continuing supply of marker dye in the flowing liquid enteral nutritional product during feeding, the dye is utilized herein in a controlled release dosage form. An example of such a dosage form that is depicted in FIG. 18 is of the osmotic pump type that functions in the manner of the osmotically driven delivery device described and claimed in U.S. Pat. No. 5,318,558, the specification and drawings of which are incorporated herein by reference with respect to the structure of the controlled release dosage form units there described and the method of making them and their mode of functioning, albeit here with different environments and contents and end uses. In the pump type osmotic dosage forms the beneficial agent(s) in liquid form, i.e., either in the liquid state or in solution in a suitable solvent, is expressed out from a cylindrical enclosure or cavity 56 within the reservoir through a small orifice 57 by the action of a piston 58 driven by pressure developed by osmotic infusion of moisture through a semi-permeable membrane 59 confining a hydro-active substance 60 behind the piston 58, driving the piston steadily toward the side of the reservoir where the ingredient(s) 61 is forced out through the orifice 57. Orifice 57 is very small and is preferably drilled by a laser beam. The cylindrical enclosure 56 is formed within a non-permeable membrane or coating 62. The hydro-active substance may be a water soluble salt like magnesium sulfate, magnesium chloride, potassium sulfate, sodium chloride, sorbitol, inositol, urea, or a saccharide such as glucose or fructose or dextran, or, a hydrophilic polymer such as a poly(hydroxyalkyl methacrylate) with a molecular weight of 30,000 to 5,000,000, poly(vinylpyrrolidone) with a molecular weight of 10,000 to 360,000, an anionic or cationic hydrogel or polyvinyl alcohol having low acetate residual.

Figure 19:
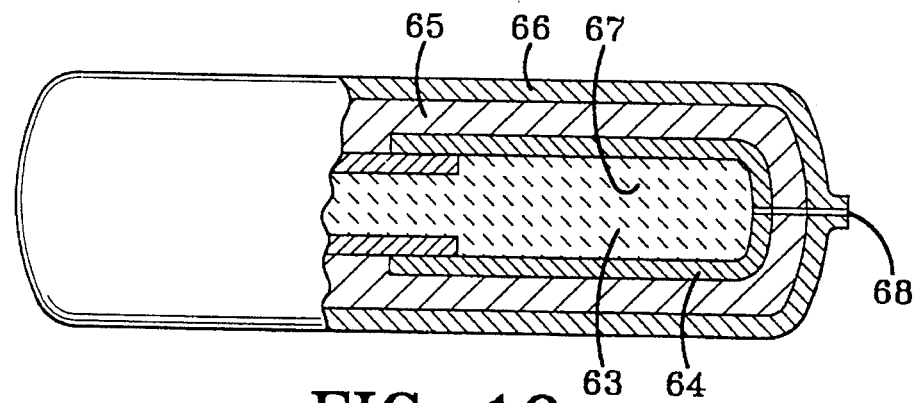
FIG. 19 is a view similar to FIG. 18 of another osmotic delivery device suitable for sustained release of a marker dye or dye mixture.

Another suitable controlled release dosage form depicted in FIG. 19 is another osmotic driven dosage system that functions in the manner of the osmotically operated delivery device described and claimed in U.S. Pat. No. 5,324,280, the specification and drawings of which are incorporated herein by reference with respect to the structure of the sustained release dosage form units there described and the method of making them and their mode of functioning, albeit here with different environments and contents and end uses. In this type of system, the beneficial agent(s) 63 to be fed in liquid state or solution form, is enclosed within a non-permeable coating 64 that is surrounded by a layer 65 of hydro-active material that is entirely confined within an outer semi-permeable membrane coating 66. Osmotic pressure developing in the hydro-active layer 65 upon infusion of moisture thereinto compresses the core 67 containing the liquid form beneficial agent(s) 63 and forces that liquid out steadily through a very small passageway 68 from the core 67 to the exterior of the unit.

Figure 19A:
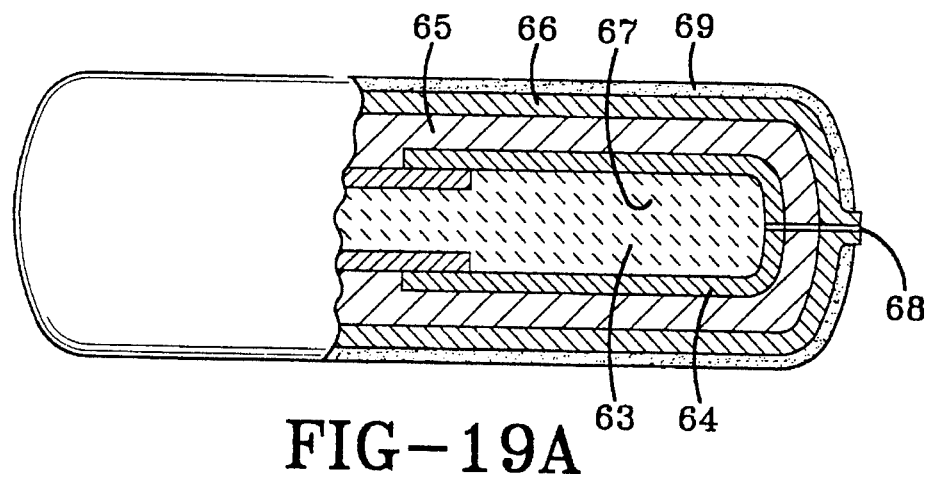
FIG. 19A is a view of the osmotic delivery device of FIG. 19 having a surface coating of a marker dye or dye mixture.

Turning now to FIG. 19A, the controlled release dosage form unit shown in either of FIGS. 18 or 19 may be coated with a readily soluble coating, such as coating 69 of marker dye, preferably a colorant marker dye, for the purpose of achieving quick initial release of enough of such dye within seconds to show initial coloration of the flowing liquid enteral nutritional product within the formulation chamber until dye starts to be expressed out of the orifice of the osmotically driven device. To apply such a coating, the marker dye is admixed with a small amount of one or more conventional easily dispersed tablet coating excipients, such as, polyvinylpyrrolidone having an average molecular weight in the range of about 35,000 to 50,000, mannitol, magnesium stearate, and small amounts of zein or guar gum, in a solvent such as water or alcohol and applied to the controlled release dosage form units as a very light coating, only tenths or hundredths of a milligram of dye usually being needed per unit. Generally the amount of excipients in total in the coating is less than about 10 percent by weight of the coating. Or, the dosage form unit may be simply wetted by an aqueous or alcoholic solution of the marker dye and dried.

The marker dye may also be employed as a tablet, a capsule, as agglomerated particles, or as microspheres, in each case coated to provide a conventional sustained release type of controlled release dosage form. Usually materials such as zein, shellac, methacrylate polymers and copolymers, and cellulose ethers and esters are used as coatings. The microspheres are microencapsulated with a range of coating layers or thicknesses of respective fractions and the fractions blended to obtain a series of delayed releases from the blend when used.

Most any mode of making a sustained or controlled release dosage form may be used in making a controlled release dosage form of marker dye that is usable according to the invention so long as the soluble, dispersible or disintegrable components of the dosage form units are physiologically acceptable and the controlled release dosage form is capable of storing one or more marker dyes as above defined and releasing the same into a liquid enteral nutritional product in a visibly detectable amount as seen under either or both of white light or ultraviolet light over a useful period of time during enteral feeding. Preferably the controlled release dosage form is an osmotically driven device because typically there is greater uniformity of release rate over time a rather long sustained release period of many hours is attainable, while the other forms may be adequate in many instances and lower in cost.

Amongst the nutrients that are most likely to be added to conventional enteral nutritional compositions according to this invention are nutrients, such as, glutamine, vitamins, arginine, fermentable dietary fibers, non-fermentable dietary fibers, enzymes such as lipases, combinations of amino acids, oligosaccharides such as fructo-saccharides, short chain ($C_3$–$C_4$) fatty acids, pyruvate precursors such as pyruvamide, or pyruvyl-amino acids, such as, pyruvyl-glycine, pyruvyl-alanine, pyruvyl-leucine, pyruvyl-valine, pyruvyl-sarcosamine and their amides, esters and salts, structured lipids, d-cyroinositol, lactoferrin, marine oils, and acidulents such as ascorbic acid. An example of a structured lipid which provides excellent nutritional support is a glycerol backbone with at least one gamma linolenic acid or dihomogamma-linolenic acid residue in combination with a medium chain ($C_6$–$C_2$) fatty acid residue and a $C_{18}$–$C_{22}$ n–3 fatty acid residue selected from alpha-linolenic and stearodonic, eicosapentaenoic and docosahexaenoic acid.

Medicaments that may be usefully administered in this manner include, e.g., antihistamine drugs; anti-infective agents, such as antibiotics, antivirals and urinary tract anti-infectives; antineoplastic agents; autonomic drugs such as adrenergic agents and skeletal muscle relaxants; blood formation and coagulation drugs; cardiovascular drugs; central nervous system agents; diagnostic agents; electrolytic, caloric and water balance agents; enzymes; antitussive, expectorant and mucolytic agents; gastrointestinal drugs such as antacids; gold compounds; hormones and synthetic substitutes; smooth muscle relaxants; and unclassified therapeutic agents. Other examples are H2 blockers like Tagamet®, prokinetic medications, bioactive peptides, medication for diabetic condition, chemotherapy agents, or any medication intended for oral administration that will not react adversely with the nutritional formulation being fed into the gastrointestinal tract.

Probiotics that may be usefully administered in this manner include, for example, *Lactobacillus acidophilus* GG, as described in U.S. Pat. No. 4,839,281, *Lactobacillus reuteri, Lactobacillus animalis,* and *Lactobacillus salivarius*, as described in WO 93/02558. Probiotics are live organisms that aid in the digestion of food or that help control the population of harmful microorganisms in the intestines.

A feeding set, such as the kit 20 shown in FIG. 14, is conveniently provided in packaged form ready for use in feeding a liquid enteral nutritional product. The kit includes (1) a dose unit 32 of beneficial agent, for example, in the form of an uncoated tablet, or tablets or particulated material in a tea bag type packet, (2) a formulation chamber 27 in the form of a drip chamber, and (3) liquid communication means 28 consisting mainly of a length of flexible tubing 54 attached at one end to the outlet 29 of the formulation chamber 27 and at the other end to a fitting 30 for coupling attachment to a feeding tube. The dose unit 32 of beneficial agent has already been placed in the formulation chamber 27 and contains one or more beneficial agents as defined hereinabove for modification of a liquid enteral nutritional product during feeding thereof. The kit may also be provided with a plurality of dose units 32 of the same or different beneficial agents within the formulation chamber 27 if a single dose unit 32 does not contain each type of beneficial agent desired for modification of the nutritional product. A marker dye in controlled release dosage form may also be added to the formulation chamber or if it is desired to utilize a marker dye during feeding.

A similar kit 20a, as shown in FIG. 15, includes a dose unit 32 of beneficial agent which has not been placed in the formulation chamber 27 before shipping the kit, but may accompany the formulation chamber, ordinarily packaged as a complete feeding set ready-to-hang as soon as the dose unit 32 is placed in the formulation chamber. Any of the types of dose units 32 herein described and containing one or more additional and various selected beneficial agents may also be placed in the formulation chamber, if desired, before use.

In a preferred embodiment of the apparatus and method of the invention, the apparatus illustrated in FIG. 2 is provided and assembled with a formulation chamber such as drip chamber 27 having positioned therein five 4 gram tablets of glutamine, free of any controlled release coating or other mechanism, as the dose units 32 of beneficial agent. The drip chamber 27 also is provided with a controlled release dosage form similar to the osmotically driven device shown in FIG. 19A containing about 375 mg of F.D.& C. Blue #1 dye in fine micronized particulate form. The controlled release dosage form is also externally coated with a thin layer of the same blue dye admixed with about 3 percent by weight in total of polyvinylpyrrolidone having an average molecular weight in the range of about 35,000 to 44,500. Fluid communication means such as communication means 28 is attached to the outlet 29 of the formulation chamber and connected to a volume flow metering device. The drip chamber of the feeding kit is connected to a hanging supply container of a liquid enteral nutritional product having a viscosity of about 40 cps., such as PULMOCARE®, a product of the Ross Products Division Abbott Laboratories, Columbus, Ohio, and a steady stream of the nutritional product is commenced. The uncoated 4 gram tablets of glutamine dissolve in the flow of the nutritional product during about six hours, thus supplementing the nutrient content thereof. The dye coating provides immediate visible color within the drip chamber within about 2 seconds and the controlled release dosage form of the blue dye provides the dye in a visible concentration of at least 0.075 mg/ml for a period of over 1,440 minutes during the flow of about 3,000 ml of the liquid enteral nutritional product.

The foregoing embodiment is repeated in a very similar manner except that a dose 32 consisting of 25 grams of fine particulate glutamine enclosed in a fibrous tea bag type carrier is positioned in the drip chamber 27 along with the blue marker dye in the blue dye-coated osmotically driven device. The same liquid enteral nutritional product is flowed in the same amount at the same rate with closely similar results, except that the 25 gram quantity of glutamine in the tea bag type carrier dissolves in the flow of the nutritional product during about eight hours, thus supplementing the nutrient content of the liquid enteral nutritional product.

We claim:

1. An apparatus for modifying a liquid enteral nutritional product during the feeding thereof comprising:

a formulation chamber having an inlet and an outlet, the inlet being located at the top of the formulation chamber and the outlet being located at the bottom of the formulation chamber with the inlet connected to a supply container of a liquid enteral nutritional product having viscosity in the range of about 5 to about 300 centipoises so as to receive said product thereof, at least one dose unit of a beneficial agent in at least a dosage amount being disposed within the formulation chamber so as to be wetted by or immersed in the liquid enteral nutritional product traversing therethrough from the inlet to the outlet of the formulation chamber, each at least one beneficial agent in the dose unit being selected from the group consisting of: nutrients; medicaments; probiotics; and diagnostic agents; and chemically and physiologically compatible combinations thereof; each dose unit of beneficial agent disposed in the formulation chamber being not in controlled release form and being a means for providing and dispensing the beneficial agent into said liquid enteral nutritional product when the dose unit is physically contacted thereby during the feeding thereof into the gastrointestinal tract of a patient over a time period of less than 2 hours; and fluid communication means capable of operatively connecting the outlet of the formulation chamber to a device which feeds the liquid enteral nutritional product into the gastrointestinal tract of a patient.

2. The apparatus of claim 1 wherein the formulation chamber is a drip chamber.

3. The apparatus of claim 1 wherein the formulation chamber has disposed therein a plurality of beneficial agents each in dose unit amount.

4. The apparatus of claim 1 wherein the beneficial agent disposed within the formulation chamber comprises at least one nutrient selected from the group consisting of glutamine, arginine, vitamins fermentable dietary fibers, non-fermentable dietary fibers, enzymes, combinations of amino acids, oligosaccharides, short chain ($C_3$–$C_4$) fatty acids, pyruvate precursors and their amides, esters and salts, structured lipids, d-cyroinositol, lactoferrin, marine oils and acidulants.

5. The apparatus of claim 4 wherein the beneficial agent disposed within the formulation chamber comprises glutamine.

6. The apparatus of claim 1 wherein the beneficial agent disposed within the formulation chamber comprises at least one medicament selected from the group consisting of antacids, antibiotics, prokinetic medications, bioactive peptides, medication for diabetic condition, chemotherapy agents, or any other medication intended for oral administration that will not react adversely with the enteral nutritional product being fed into the gastrointestinal tract.

7. The apparatus of claim 6 wherein the beneficial agent disposed within the formulation chamber comprises a probiotic.

8. The apparatus of claim 1 wherein the beneficial agent is confined within a mesh bag within the formulation chamber.

9. The apparatus of claim 1 wherein the beneficial agent is confined within a foraminous bag within the formulation chamber.

10. The apparatus of claim 1 wherein the beneficial agent is confined within a porous fibrous envelope within the formulation chamber.

11. The apparatus of claim 10 wherein the fibrous envelope is non-woven.

12. The apparatus of claim 1 wherein the fluid communicating means includes a flexible tubing section suitable for use with a pump.

13. The apparatus of claim 1 wherein the fluid communicating means further comprises at least one additional formulation chamber having disposed therein at least one beneficial agent.

14. The apparatus of claim 1 wherein the fluid communicating means further comprises at least one additional formulation chamber having disposed therein a controlled release dosage form containing only, as the medium dispersible additive, a physiologically acceptable marker dye, said at least one sustained release reservoir containing marker dye being a means for providing and dispensing marker dye into a liquid enteral nutritional product having a viscosity in the range of about 5 to about 300 centipoises when the sustained release reservoir is physically contacted thereby during the feeding thereof to a patient over a time period of at least about 2 to about 24 hours.

15. The apparatus of claim 1 further comprising a controlled release dosage form disposed within the formulation chamber, the controlled release dosage form containing a physiologically acceptable marker dye, said at least one sustained release reservoir containing marker dye being a means for providing and dispensing marker dye into a liquid enteral nutritional product having a viscosity in the range of about 5 to about 300 centipoises when the sustained release reservoir is physically contacted thereby during the feeding thereof to a patient over a time period of at least about 2 to about 24 hours.

16. A method of modifying a liquid enteral nutritional product during the flow thereof from a supply container containing such product to a feeding tube leading into the gastrointestinal tract of a patient, comprising the steps of:
 (a) providing an apparatus comprising:
  a formulation chamber having an inlet and an outlet, the inlet being located at the top of the formulation chamber and the outlet being located at the bottom of the formulation chamber with the inlet being connectable to a supply container of a liquid enteral nutritional product so as to receive said product thereof;
  at least one dose unit of at least one beneficial agent not in controlled release dosage form, each at least one beneficial agent in the dose unit being selected from the group consisting of: nutrients; medicaments; probiotics; and diagnostic agents; and chemically and physiologically compatible combinations thereof, the at least one dose unit of beneficial agent being positioned as the only solid form beneficial agent contents in the formulation chamber and being a means for providing and dispensing the beneficial agent into said liquid enteral nutritional product having a viscosity in the range of about 5 to about 300 centipoises when the dose unit is physically contacted thereby during the feeding thereof into the gastrointestinal tract of a patient over a time period of less than 2 hours; and
  fluid communication means capable of operatively connecting the outlet of the formulation chamber to a device which feeds said liquid enteral nutritional product into the gastrointestinal tract of a patient;
 (b) providing said supply container containing said liquid enteral nutritional product having a viscosity in the range of about 5 to about 300 cps.;
 (c) placing the apparatus in communicative series in the fluid flow between said supply container and said device which feeds said liquid enteral nutritional product into the gastrointestinal tract of a patient and,
 flowing the liquid enteral nutritional product through the apparatus and into said device which feeds said liquid enteral nutritional product into the gastrointestinal tract of a patient.

17. The method of claim 16 in which the apparatus described in step (a) further comprises a controlled release dosage form disposed within the formulation chamber, the controlled release dosage form containing a physiologically acceptable marker dye, said at least one sustained release reservoir containing marker dye being a means for providing and dispensing marker dye into a liquid enteral nutritional product has a viscosity in the range of from about 5 cps. to about 300 cps when the sustained release reservoir is physically contacted thereby during the feeding thereof to a patient over a time period of at least about 2 to about 24 hours.

18. The method of claim 16 in which the liquid enteral nutritional product has a viscosity in the range of about 5 to about 150 cps.

19. The method of claim 16 in which the apparatus provided includes more than one formulation chamber and at least one beneficial agent not in controlled release dosage form and in dose unit quantity and with or without a marker dye is positioned in each formulation chamber as the only contents thereof.

20. The method of claim 18 in which the liquid enteral nutritional product has a viscosity in the range of from about 5 cps. to about 150 cps.

21. The method of claim 16 in which the apparatus provided in step (a) comprises more than one formulation chamber in series flow relationship and one of the formulation chambers contains at least one marker dye in controlled release dosage form as the only contents of the formulation chamber said at least one sustained release reservoir containing marker dye being a means for providing and dispensing marker dye into a liquid enteral nutritional product has a viscosity in the range of from about 5 cps. to about 300 cps when the sustained release reservoir is physically contacted thereby during the feeding thereof to a patient over a time period of at least about 2 to about 24 hours.

22. A method of modifying a liquid enteral nutritional product during the flow thereof from a supply container containing such product to a feeding tube leading into the gastrointestinal tract of a patient, comprising the steps of:
 (a) providing an apparatus comprising:
  a formulation chamber having an inlet and an outlet, the inlet being located at the top of the formulation chamber and the outlet being located at the bottom of the formulation chamber with the inlet being connectable to a supply container of a liquid enteral nutritional product so as to receive said product thereof; and
  fluid communication means capable of operatively connecting the outlet of the formulation chamber to a device which feeds said liquid enteral nutritional product into the gastrointestinal tract of a patient;
 (b) providing at least one dose unit of at least one beneficial agent not in controlled release dosage form said dose unit being a means for providing and dispensing the beneficial agent into said liquid enteral nutritional product having a viscosity in the range of about 5 to about 300 centipoises when the dose unit is physically contacted thereby;
 (c) positioning the at least one dose unit of beneficial agent in the formulation chamber as the only solid form beneficial agent contents therein;
 (d) providing said supply container containing a liquid enteral nutritional product having a viscosity in the range of about 5 to about 300 cps.;
 (e) placing the apparatus in communicative series in the fluid flow between said supply container and said device which feeds said liquid enteral nutritional product into the gastrointestinal tract of a patient; and,
 (d) flowing the liquid enteral nutritional product through the apparatus, thereby causing the liquid enteral nutritional product to physically contact the dose unit, and into said device which feeds said liquid enteral nutritional product into the gastrointestinal tract of a patient.

23. A drip chamber comprising an inlet and an outlet, the inlet being located at the top of the drip chamber and the outlet being located at the bottom of the drip chamber with the inlet connected to a supply container with a liquid enteral nutritional product having a viscosity in the range of about 5 to about 300 centipoises so as to receive the product thereof, said drip chamber having disposed therein at least a physiologically useful or diagnostically detectable amount of at least one beneficial agent as a dose unit, not in controlled release dosage form, each beneficial agent being selected from the group consisting of: nutrients; medicaments; probiotics; diagnostic agents; and chemically and physiologically compatible combinations thereof; each dose unit being a means for providing and dispensing the beneficial agent into said liquid enteral nutritional product when the dose unit is physically contacted thereby during the feeding thereof into the gastrointestinal tract of a patient over a time period of less than 2 hours.

24. The drip chamber as in claim 23 further comprising at least one marker dye in controlled release dosage form said controlled release dosage form being a means for providing and dispensing marker dye into a liquid enteral nutritional product which has a viscosity in the range of from about 5 cps. to about 300 cps when the controlled release dosage form is physically contacted thereby during the feeding thereof to a patient over a time period of at least about 2 to about 24 hours.

25. A kit for feeding liquid enteral nutritional product into the gastrointestinal tract of a patient, comprising:

a formulation chamber having an inlet and an outlet and, the inlet being located at the top of the drip chamber and the outlet being located at the bottom of the drip chamber with the inlet connected to a supply container with a liquid enteral nutritional product having a viscosity in the range of about 5 to about 300 centipoises so as to receive said product;

at least one beneficial agent in dose unit form being disposed within the formulation chamber so as to be wetted by or immersed in liquid enteral nutritional product traversing therethrough, each at least one beneficial agent being selected from the group consisting of: nutrients; medicaments; probiotics; and diagnostic agents; and chemically and physiologically compatible combinations thereof; being a means for providing and dispensing the beneficial agent into said liquid enteral nutritional product when the dose unit is physically contacted thereby during the feeding thereof into the gastrointestinal tract of a patient over a time period of less than two hours; and fluid communication means capable of operatively connecting the outlet of the formulation chamber to a tube for feeding into the gastrointestinal tract of a patient.

26. The kit of claim 25 wherein the at least one beneficial agent is not positioned in the formulation chamber but is packaged together therewith.

* * * * *

UNITED STATES PATENT AND TRADEMARK OFFICE
CERTIFICATE OF CORRECTION

PATENT NO. : 5,533,973
DATED : June 9, 1996
INVENTOR(S) : Piontek, et. Al.

It is certified that error appears in the above-indentified patent and that said Letters Patent is hereby corrected as shown below:

Column 17, line 57, change "of" to --with--.

Column 17, line 58, change "viscosity" to --a viscosity--.

Column 19, line 54, change "patient" to --patient;--.

Column 21, line 6, change "the" to --said--.

Column 22, line 16, change "thereof; being" to --thereof; each dose unit of beneficial agent being--.

Signed and Sealed this

Fourteenth Day of January, 1997

Attest:

BRUCE LEHMAN

*Attesting Officer*     *Commissioner of Patents and Trademarks*